(12) United States Patent　(10) Patent No.: US 10,674,918 B2
Godavarty et al.　(45) Date of Patent: Jun. 9, 2020

(54) NEAR-INFRARED (NIR) OPTICAL SCANNER

(71) Applicant: THE FLORIDA INTERNATIONAL UNIVERSITY BOARD OF TRUSTEES, Miami, FL (US)

(72) Inventors: Anuradha Godavarty, Miami, FL (US); Youngjin Jung, Miami, FL (US); Jean Gonzalez, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 596 days.

(21) Appl. No.: 14/370,600

(22) PCT Filed: Jan. 7, 2013

(86) PCT No.: PCT/US2013/020461
§ 371 (c)(1),
(2) Date: Jul. 3, 2014

(87) PCT Pub. No.: WO2013/103935
PCT Pub. Date: Jul. 11, 2013

(65) Prior Publication Data
US 2014/0364743 A1　Dec. 11, 2014

Related U.S. Application Data

(60) Provisional application No. 61/650,296, filed on May 22, 2012, provisional application No. 61/583,730, filed on Jan. 6, 2012.

(51) Int. Cl.
*A61B 5/00* (2006.01)
*G01N 21/359* (2014.01)
(Continued)

(52) U.S. Cl.
CPC .......... *A61B 5/0071* (2013.01); *A61B 5/0073* (2013.01); *A61B 5/0091* (2013.01);
(Continued)

(58) Field of Classification Search
CPC ... A61B 5/0071; A61B 5/0073; A61B 5/0091; A61B 5/4312; A61B 2560/0431;
(Continued)

(56) References Cited

U.S. PATENT DOCUMENTS 5,730,133 A　3/1998　Godik
5,830,145 A　11/1998　Tenhoff
(Continued)

FOREIGN PATENT DOCUMENTS

DE　102005058598 A1　7/2006
EP　1797818 A2　6/2007
(Continued)

OTHER PUBLICATIONS

International Preliminary Report on Patentability and Written Opinion issued in PCT/US2013/020461 dated Jul. 8, 23014.
(Continued)

*Primary Examiner* — Jeffrey G Hoekstra
*Assistant Examiner* — Patrick M Mehl
(74) *Attorney, Agent, or Firm* — Marshall, Gerstein & Borun LLP

(57) ABSTRACT

A method, apparatus, and system acquire data to create a 3D mesh representing a 3D object. The method, apparatus, and system acquire image data of the 3D object using an imaging probe that includes illumination and detection capability. A light source operates to illuminate the 3D object for reflection and/or trans-illumination imaging, and a detection assembly receives image reflection and/or trans-illumination image data. The reflectance and trans-illumination image data collected by the detection assembly are co-registered
(Continued)

with a previously acquired 3D mesh using data from a tracking system monitoring the position of the probe, displayed in real-time, and optionally saved.

15 Claims, 17 Drawing Sheets

(51) Int. Cl.
*G01N 21/49* (2006.01)
*G01N 21/64* (2006.01)
*G01N 21/59* (2006.01)

(52) U.S. Cl.
CPC .......... *G01N 21/359* (2013.01); *G01N 21/49* (2013.01); *G01N 21/6456* (2013.01); *A61B 5/4312* (2013.01); *A61B 2560/0431* (2013.01); *G01N 2021/5957* (2013.01)

(58) Field of Classification Search
CPC .. G01N 21/6456; G01N 21/49; G01N 21/359; G01N 2021/5957
See application file for complete search history.

(56) References Cited

U.S. PATENT DOCUMENTS

| | | | |
|---|---|---|---|
| 5,971,997 A | 10/1999 | Guthrie et al. | |
| 5,983,122 A | 11/1999 | Jarman et al. | |
| 6,795,195 B1 | 9/2004 | Barbour et al. | |
| 6,808,289 B2 * | 10/2004 | Reed | F21S 9/02 362/198 |
| RE38,800 E | 9/2005 | Barbour | |
| 8,070,682 B2 | 12/2011 | Zhu | |
| 8,712,504 B2 | 4/2014 | Godavarty et al. | |
| 2002/0035317 A1 | 3/2002 | Cheng et al. | |
| 2002/0045811 A1 | 4/2002 | Kittrell et al. | |
| 2002/0050988 A1 | 5/2002 | Petrov et al. | |
| 2004/0215072 A1 | 10/2004 | Zhu | |
| 2004/0254464 A1 | 12/2004 | Stribling | |
| 2005/0004453 A1 | 1/2005 | Tearney et al. | |
| 2005/0116179 A1 | 6/2005 | Aguirre et al. | |
| 2007/0219450 A1 | 9/2007 | Azar et al. | |
| 2008/0294056 A1 * | 11/2008 | Boutet | A61B 90/36 600/476 |
| 2009/0137908 A1 * | 5/2009 | Patwardhan | A61B 5/0059 600/476 |
| 2009/0240145 A1 | 9/2009 | Otsuka | |
| 2009/0306521 A1 | 12/2009 | Ermakov et al. | |
| 2010/0010340 A1 | 1/2010 | Godavarty et al. | |
| 2010/0078576 A1 | 4/2010 | Ntziachristos et al. | |
| 2010/0155599 A1 * | 6/2010 | Godavarty | A61B 5/0091 250/334 |
| 2010/0256496 A1 | 10/2010 | Zhu | |
| 2010/0324423 A1 | 12/2010 | El-Aklouk et al. | |
| 2011/0190639 A1 * | 8/2011 | Peltie | A61B 5/0059 600/476 |
| 2011/0229840 A1 * | 9/2011 | Liang | A61B 5/1077 433/29 |
| 2012/0271129 A1 | 10/2012 | Wang | |
| 2013/0109941 A1 | 5/2013 | Li et al. | |
| 2013/0169759 A1 | 7/2013 | Godavarty et al. | |
| 2015/0190061 A1 | 7/2015 | Godavarty et al. | |

FOREIGN PATENT DOCUMENTS

| | | | | |
|---|---|---|---|---|
| EP | 2 319 406 A1 | 5/2011 | | |
| WO | WO-94/24927 A1 | 11/1994 | | |
| WO | WO 1994024927 A1 * | 11/1994 | ............... | A61B 5/00 |
| WO | WO-2008/039988 A2 | 4/2008 | | |
| WO | WO-2011/156810 A2 | 12/2011 | | |

OTHER PUBLICATIONS

Culver et al., Three-Dimensional Diffuse Optical Tomography in the Parallel Plane Transmission Geometry: Evaluation of a Hybrid Frequency Domain/Continuous Wave Clinical System for Breast Imaging, *Medical Physics*, 30(2):235-47 (Feb. 2003).
Ge et al., A Novel Optical Imager Towards Breast Cancer Diagnosis, *Medical Physics*, 33(6):1989 (Jun. 2006).
Godavarty et al., Fluorescence-Enhanced Optical Imaging of Large Phantoms Using Single and Simultaneous Dual Point Illumination Geometries, *Medical Physics*, 31(2):183-90 (Feb. 2004).
Jayachandran et al., Design and Development of a Hand-Held Optical Probe Toward Fluorescence Diagnostic Imaging, *J. Biomedical Optics*, 12(5):054014-1-10 (2007).
Regalado et al., Automated coregistered imaging using a hand-held probe-based optical imager, Rev. Sci. Instrum., 81:023702 (2010).
Extended European Search Report, European patent application No. EP13733558.4, dated Aug. 7, 2015.
Zhu et al., Ultrasound-guided optical tomographic imaging of malignant and benign breast legions: initial clinical results of 19 cases, Neoplasia, 5(5):379-86 (2003).
Examination Report for European Application No. 11793309.3, dated Jul. 11, 2017.
Partial Supplementary European Search Report for Application No. EP 15733318.8, dated Aug. 18, 2017.

\* cited by examiner

| Imaging Modality | Principle | Advantages | Disadvantages |
|---|---|---|---|
| X-ray | Uses x-rays of ~ 50 KeV photons to detect the x-rays attenuated by tissues of differing densities | Excellent resolution<br>Good penetration depth | Ionizing radiation<br>Poor contrast among soft tissues<br>Overlooks 10% of breast cancer in non-calcified lesions |
| Computer Tomography (CT) | Uses x-rays at different angles for cross-sectional views | Same as x-ray technique, but provides more information | Greater exposure to x-ray radiation |
| Ultrasound (US) | Uses high frequency sound waves to detect the reflectance and transmittance from acoustically dissimilar tissues | Non-ionizing radiation<br>Inexpensive<br>Portable, safe, and versatile | Poor imaging quality<br>Poor contrast |
| Magnetic resonance imaging (MRI) | Uses strong magnetic fields and RF waves to detect the emitted RF waves and relaxation of spin state of nuclei in tissues | Non-ionizing radiation<br>Functional imaging<br>Soft-tissue contrast<br>Good resolution<br>Good penetration depth | Strong magnetic field<br>Expensive<br>Not portable<br>Slow process |

FIG. 1

NEAR-INFRARED (NIR) OPTICAL SCANNER

RELATED APPLICATIONS

This application claims priority to U.S. Provisional Patent application 61/583,730, filed Jan. 6, 2012, and to U.S. Provisional Patent application 61/650,296, filed May 22, 2012, the contents of which are hereby incorporated in their entirety by reference herein.

STATEMENT REGARDING FEDERALLY SPONSORED RESEARCH OR DEVELOPMENT

This invention was made with government support under R15-CA119253, awarded by the National Institutes of Health. The government has certain rights in the invention.

BACKGROUND

Existing diagnostic imaging techniques of breast cancer include X-ray mammography, computer tomography (CT), ultrasound, magnetic resonance imaging (MRI), and nuclear imaging. FIG. 1 illustrates a table summarizing the advantages and disadvantages of each existing diagnostic imaging process or technique. These conventional techniques may be limited by poor resolution, use of harmful ionizing radiation, lack of portability, and/or expensive instrumentation.

Diffuse optical imaging (DOI) (also known as Near-infrared (NIR) optical imaging) is an emerging non-invasive technology that may be applied towards deep tissue imaging, with one application being breast cancer diagnostics However, the existing NIR optical imaging systems may be limited in a number of ways. For example, existing NIR imaging apparatus may be large and bulky systems, and thus, not generally portable. NIR imaging apparatus may also cause patient discomfort because the apparatus may require a patient to be placed in certain positions or may require compression of patient tissue. Moreover, conventional NIR imaging apparatus and methods may be limited to imaging only fixed volumes or certain shapes of breast tissue.

In recent years, hand-held probe based optical imaging systems have been developed for clinical applications. These hand-held probe based systems represent an alternative to the conventional bulky optical imaging systems. However, the available hand-held optical imagers employ contact imaging that is impractical for many applications (e.g., surgical settings, imaging of open wounds, etc.), require multiple probes, and/or are incapable of performing both trans-illumination and reflective imaging. In part because many of the

SUMMARY

An imager includes an assembly forming a hand-held probe. The hand-held probe includes a probe body and a detector assembly that includes a detector operable to capture a focused, non-point image in the near infrared spectrum. The probe also includes a source assembly including near infrared light source, and a tracking target. The near infrared light source is movable relative to the detector such that the probe can perform both reflectance and trans-illumination measurements. In addition to the assembly forming the hand-held probe, the imager includes a processor configured to capture image data from the detector assembly and to co-register the image data with a 3D mesh.

DESCRIPTION OF THE DRAWINGS

FIG. 1 illustrates a table of existing tumor diagnostic methods indicating principle of operation, advantages and disadvantages;

DETAILED DESCRIPTION

General Principles of Diffuse Optical Imaging

Figure 2:
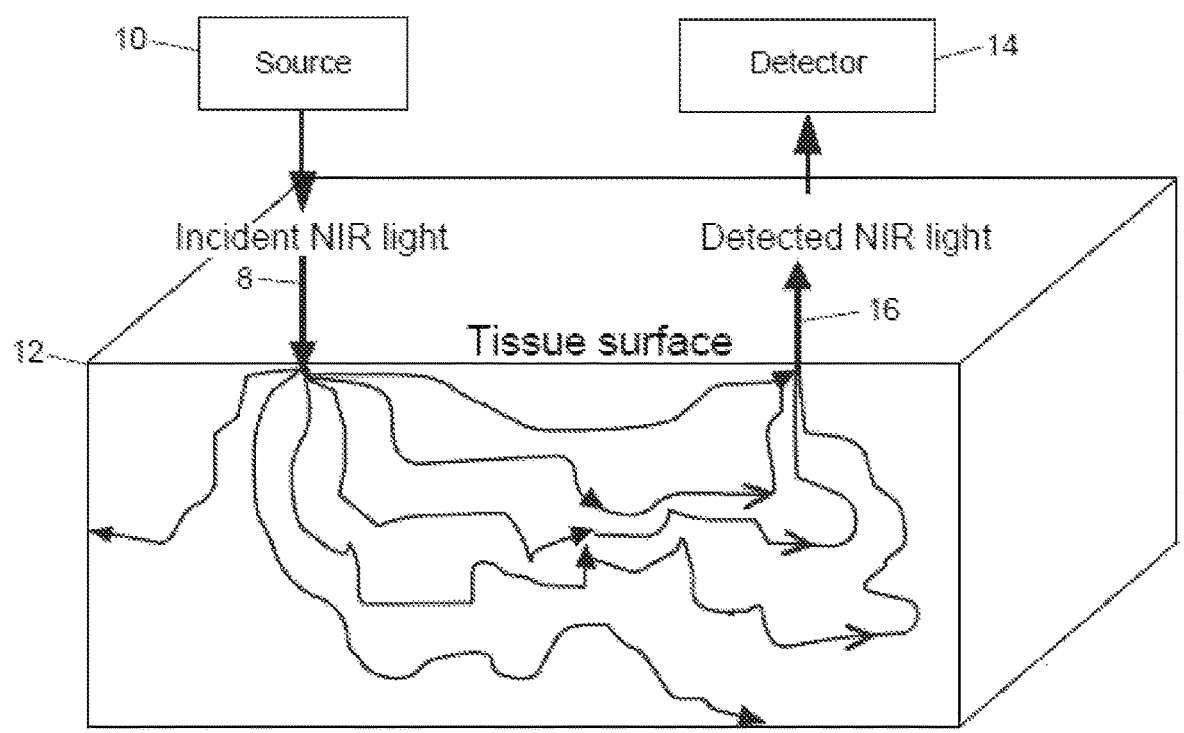
FIG. 2 illustrates a general optical imaging process.

FIG. 2 illustrates general principles behind an optical imaging process. Light 8 from a source 10 is projected on a target tissue 12 at a wavelength in the NIR spectrum. The tissue 12 may minimally absorb the light 8 while reflecting and scattering a majority of the light. A corresponding light detector 14 may be positioned to measure characteristics of the reflected light 16, such as intensity, phase, or time delay.

Generally, when NIR light is launched onto a tissue surface, light propagates into the tissue and is minimally absorbed (in biological tissues, hemoglobin and water are least absorbent in the near-infrared spectrum) and preferentially scattered, allowing deep penetration of the light into the tissue and providing an opportunity for diagnostic imaging. The reflected light and/or trans-illuminated light (i.e., light that enters tissue at a first surface and exits the tissue at a second surface opposite the first surface) may be collected at a set of point locations or by an imaging device (e.g., a charge-coupled device) on or near the tissue surface. From the collected reflected or trans-illuminated measurements, images of scattering ($\mu_s$) and absorption ($\mu_a$) coefficients of the entire tissue domain may be generated using appropriate light propagation models and reconstruction algorithms (discussed further below). Diffuse optical imaging enables translation of the highly scattered light signals into clinically meaningful information about human tissue.

For example, optical properties may be used to locate and identify physiological changes in the tissue that may indicate the existence and/or location of tumors.

Figure 3:
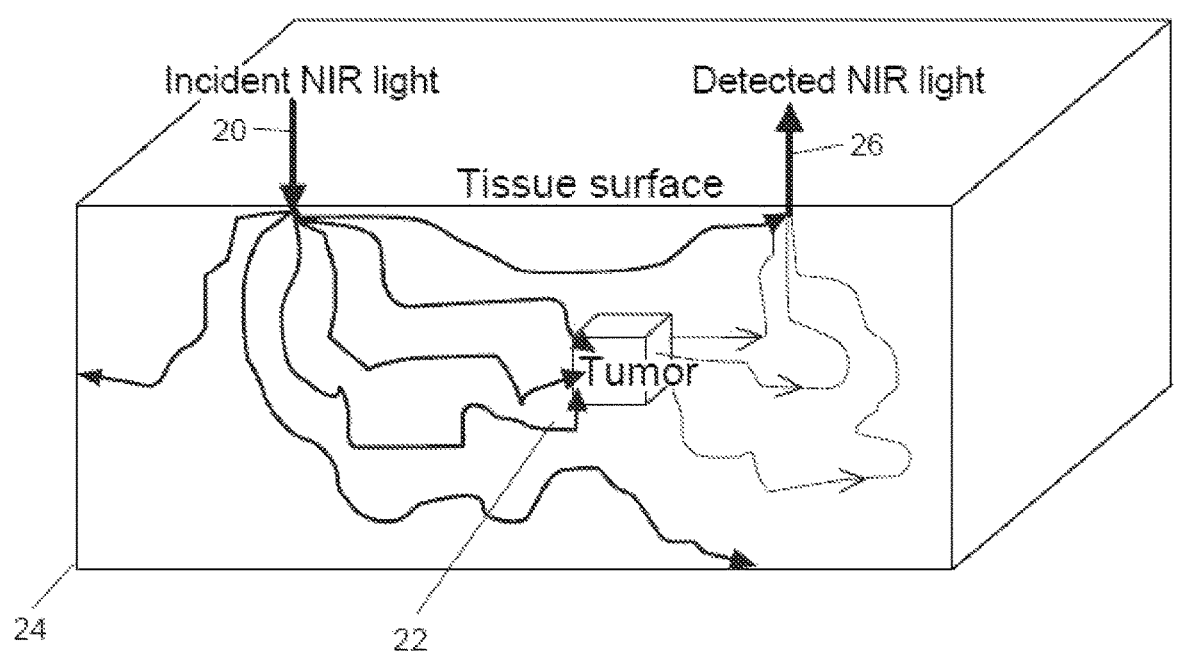
FIG. 3 illustrates a general optical imaging process in tumor detection.

Differences in composition of the tissue may cause a difference in the light characteristics (e.g., in terms of reflected/trans-illuminated light intensity, phase, time delay, etc.) of the imaging data collected. This difference in light characteristics may be used to determine abnormal tissue growth. For example, optical imaging may be used to detect a breast tumor in a chemical environment by looking for two intrinsic cancer signatures: increased blood flow (as shown by the total hemoglobin concentration) and hypermetabolism (as shown by a drop in oxygen concentration). As illustrated in FIG. 3, when NIR light 20 encounters an angiogenic (growth of blood vessels from surrounding tissue to solid tumors) region 22 of a breast tissue 24, light may be absorbed based on the different concentrations of hemoglobin in that area of the breast, thus providing endogenous contrast between normal and tumor tissue. The difference in light characteristics of the collected diffused light 26 may reflect the difference in absorption and/or scattering arising from this angiogenic region 22.

To detect tissue features (such as lesions, blood flow, etc.) smaller than about 0.5 cm (in diameter), and/or tissue features deeper within the tissue, external contrast agents may need to be used in order to improve the optical contrast between normal and diseased tissues in a process known as fluorescence-enhanced optical imaging. Fluorescence-enhanced optical imaging involves the administration of exogenous fluorescent contrast agents that specifically bind to target tissue (e.g., tumor tissue) and that are excitable in the NIR wavelength range. The external fluorescent contrast agents molecularly target the metastatic cancer cells within the breast tissue and enhance the optical contrast between the cancerous cells and the background breast tissue.

Figure 4:
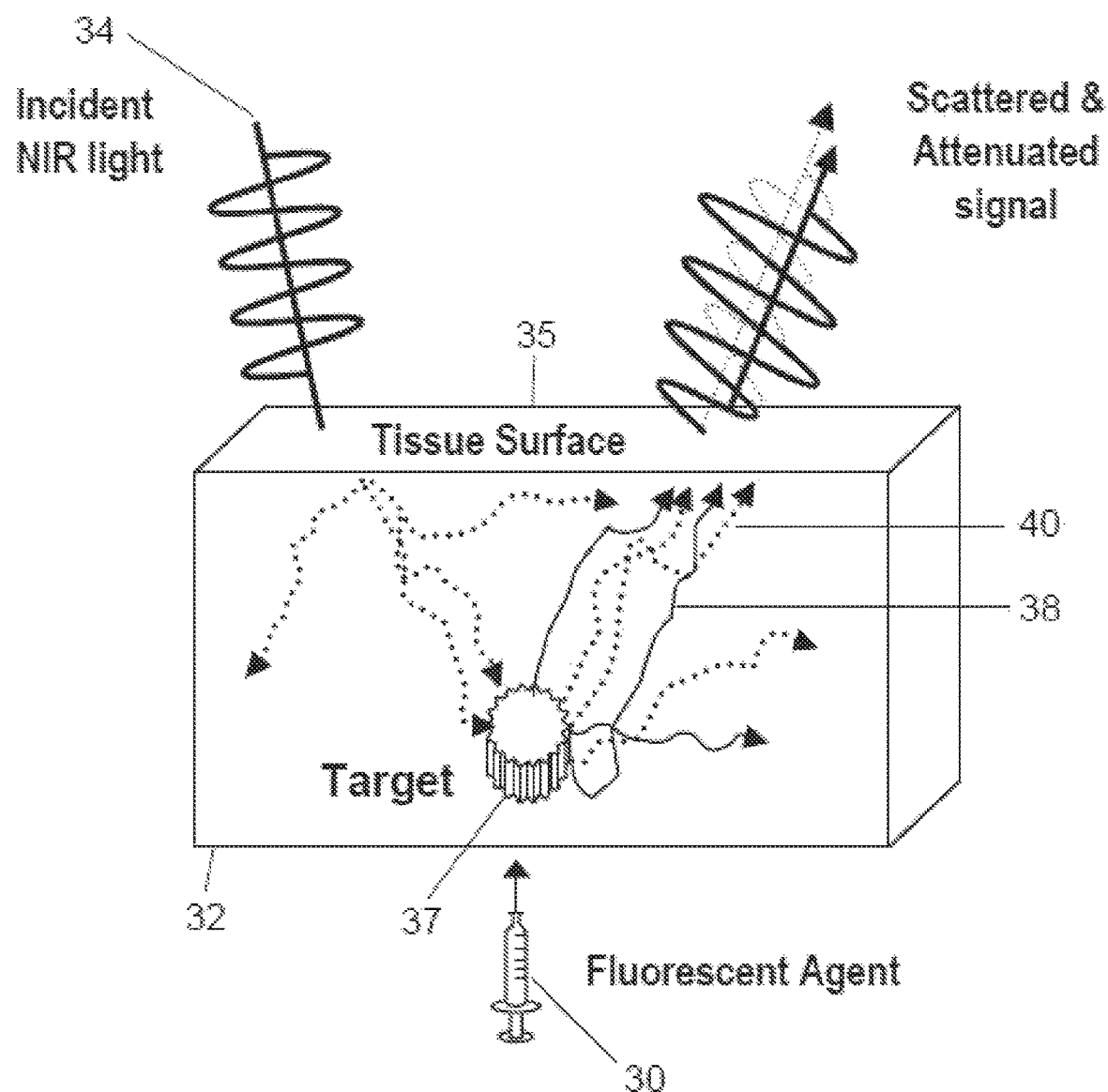
FIG. 4 illustrates a fluorescence enhanced optical imaging process.

FIG. 4 illustrates a fluorescence-enhanced optical imaging process. In a fluorescence-enhanced optical imaging process, a target-specific florescent contrast agent 30 may be injected into the tissue 32. When NIR light 34 is launched at the tissue surface 35, the minimally-absorbed and preferentially-scattered excitation photons propagate deep into the tissue 32. Upon encountering a fluorescent molecule 37 (e.g., found at the site of target tissue substructure), the photons excite the fluorescent molecule 37 from its ground state to a higher orbital level. After residing at the higher energy orbital for a period (known as the fluorescence lifetime), the fluorescent molecule emits a fluorescent signal 38 at a greater wavelength than the incident NIR light 34. The emitted fluorescent signal 38 along with the attenuated excitation signal 40 (which is at the same wavelength as the incident light) propagates back through the tissue surface where it is detected. At a detection site or device (not shown in FIG. 4), appropriate optical filters may be used to separate the fluorescence signal from the attenuated excitation signal to provide relevant light characteristic data. FIG. 4 depicts the NIR light 34 as a modulated signal (i.e., implementing a frequency-domain analysis), however the analysis may be conducted in the time domain, in the frequency domain, or in a continuous wave implementation.

Measurement Techniques

Three distinct measurement techniques may be used to process the collected light characteristic data in optical imaging. These techniques include continuous wave, time-domain photon migration (TDPM), and frequency-domain photon migration (FDPM) based imaging. Each of these measurement techniques has advantages and disadvantages, and the selection of the appropriate technique largely depends on the specific application and requirement.

Continuous wave (CW) measurement technique uses steady state light of constant intensity on the tissue surface and measures the attenuated intensity of the trans-illuminated and/or reflected light. In continuous wave based fluorescent optical imaging the NIR light attenuates due to absorption and scattering in the tissue medium. Upon encountering the florescent molecule, a steady state florescent signal is emitted, which attenuates before it is detected at the tissue surface. Continuous wave-based imaging instrumentation is relatively simple and involves low-cost optical components. The major disadvantages of continuous wave measurement technique include difficulty in resolving tissue absorption from scattering and inability to image the fluorescence decay kinetics. When independent measurements of tissue optical properties (i.e. absorption, scattering or fluorescence lifetime) and/or depth information are required, the use of TDPM or FDPM measurement techniques may be necessary.

TDPM measurement techniques illuminate tissue with ultra fast (e.g., in the femtosecond to picosecond time range) photon pulses and resolve the arrival of the photons as a function of time at different locations around the tissue boundary. In a TDPM-based fluorescence optical imaging process the excitation light pulse broadens and attenuates as it travels through the scattering medium. Upon encountering a fluorescent molecule, a fluorescent light pulse is emitted, which broadens and attenuates as it propagates in the tissue medium. This broadened pulse of fluorescent light is further broadened and attenuated due to absorption and scattering in the tissue medium, before it is detected at the tissue surface using, for example, fluorescence optical imaging.

The TDPM measurement technique may provide better depth information compared to a continuous wave measurement technique. Although TDPM-based measurements provide a wealth of information that may be used to map optical properties of tissues, TDPM measurement techniques may be limited by their large signal-to-noise ratio (SNR) range, which may require significant data acquisition times compared to CW and FDPM measurement techniques.

In FDPM-based fluorescence optical imaging, modulated excitation light is launched onto the tissue surface and the modulated fluorescent signal is detected at the tissue surface in terms of amplitude and phase shift. Measurements of the light intensity and the phase shift of the photon wave-front are obtained with respect to the source light information about the tissue optical properties and fluorochrome distribution. Frequency domain measurement technique may be preferable over TDPM measurement technique due to its inexpensive instrumentation. In addition, the steady-state FDPM measurements in terms of amplitude and phase shift are minimally corrupted by ambient light, since the instrument detects only a modulated signal. Thus, the FDPM instrument automatically acts as a filter for ambient light rejection, which is an advantage of FDPM measurement techniques over continuous wave or TDPM measurement techniques. However, FDPM measurement techniques require frequencies of several hundred MHz or higher to achieve depth information that may be difficult to obtain using continuous wave technique. In practice, usually a single frequency may be employed, and the phase shift may be used to estimate the mean time of flight of the photons. However, data obtained at multiple frequencies may improve FDPM imaging performance and may be equivalent to TDPM data via the inverse Fourier Transform.

While some embodiments are described as implementing fluorescence-based imaging, it should be understood that any of the embodiments herein may implement imaging with or without fluorescence and, in particular, may implement NIR imaging in addition to, or instead of, fluorescence based imaging.

Source and Detector Configurations for Diffuse Optical Imaging

NIR-based imaging approaches, whether based on endogenous or exogenous contrast, involve trans-illumination and/or reflection measurements. These measurements represent the light propagation between light sources and detector sensor pairs, and are based on excitation illumination and excitation/emission detection. Generally, trans-illumination is the shining of a light through a target tissue, such as breast tissue, to observe the absorption pattern from a different surface of the tissue medium. Reflection measurements involve observing light reflected off a tissue surface from the same side as the incident light.

Generally, existing optical imaging configurations for arranging sources (for providing incident/excitation signals) and detectors (for collecting reflected and/or trans-illuminated NIR signals, fluorescence or non-fluorescence signals) may be broadly categorized into projection shadow, circular, and sub-surface/reflective configurations.

Figure 5:
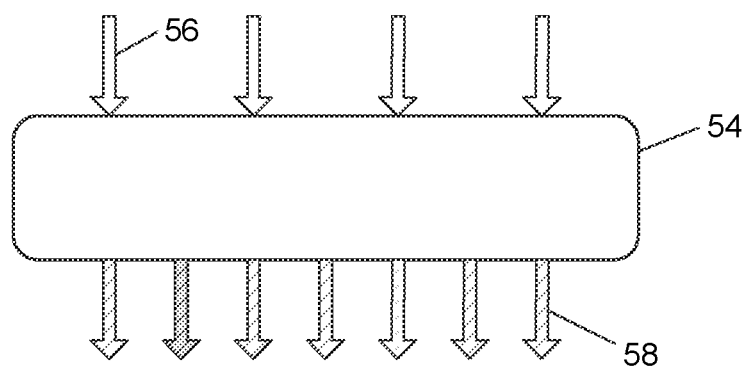
FIG. 5 illustrates a projection-shadow optical imaging process.

FIG. 5 illustrates a projection-shadow optical imaging process. Projection-shadow imaging involves collecting trans-illuminated light from the tissue object. Trans-illuminated light may refer to light that traverses a surface(s) of a tissue. In trans-illumination method, sources 56 and detectors 58 are placed on opposite sides of breast tissue 54. In this geometry, single/multiple sources may be deployed on other areas of the subject tissue so that light passes through the tissue before reaching the detector(s). Optical properties of the three dimensional tissue are obtained between the source and the detector planes. This method generally requires compression of the target tissue. The compressed tissue configuration may be analogous to x-ray mammography, and may be disadvantageous due to patient discomfort caused by tissue compression and due to limited information obtained for the entire breast tissue.

Figure 6:
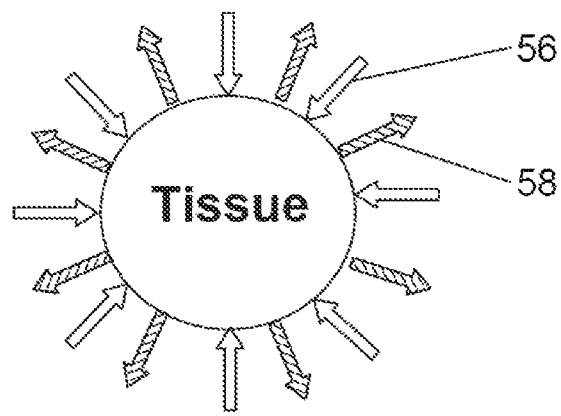
FIG. 6 illustrates a circular imaging process.

FIG. 6 illustrates a circular imaging process, wherein both the reflected and trans-illuminated light is collected along a circular circumference of the tissue. In this configuration, multiple sources 56 and detectors 58 are disposed about the circular circumference of the tissue. The circular configuration may be minimally uncomfortable to a patient, but is limited by the bulky and non-portable size of the apparatus.

Figure 7:
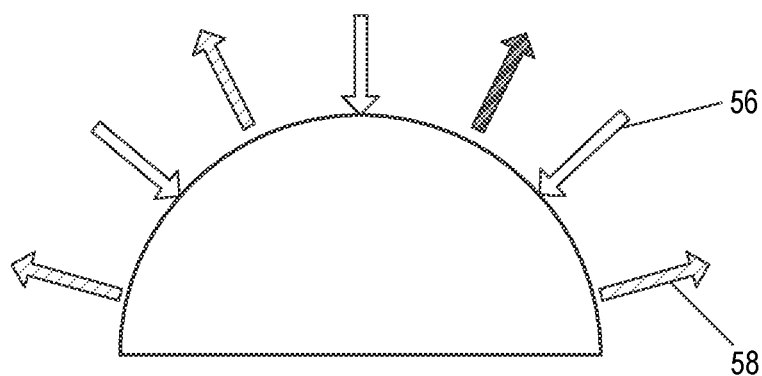
FIG. 7 illustrates general sub-surface imaging.

FIG. 7 illustrates sub-surface imaging, which may involve collecting reflected and/or trans-illuminated light using multiple sources 56 and detectors 58. This configuration requires no tissue compression, and may be designed to mimic a hand-held imaging probe. Many known commercial optical imaging systems and hand-held probes developed using the sub-surface imaging configuration are designed to only collect reflected light using flat measurement probe heads.

While the principles above are described with reference to multiple sources and multiple detectors, the principles nevertheless also apply to area source and area detector systems.

Optical Imager Assembly

Figure 8:
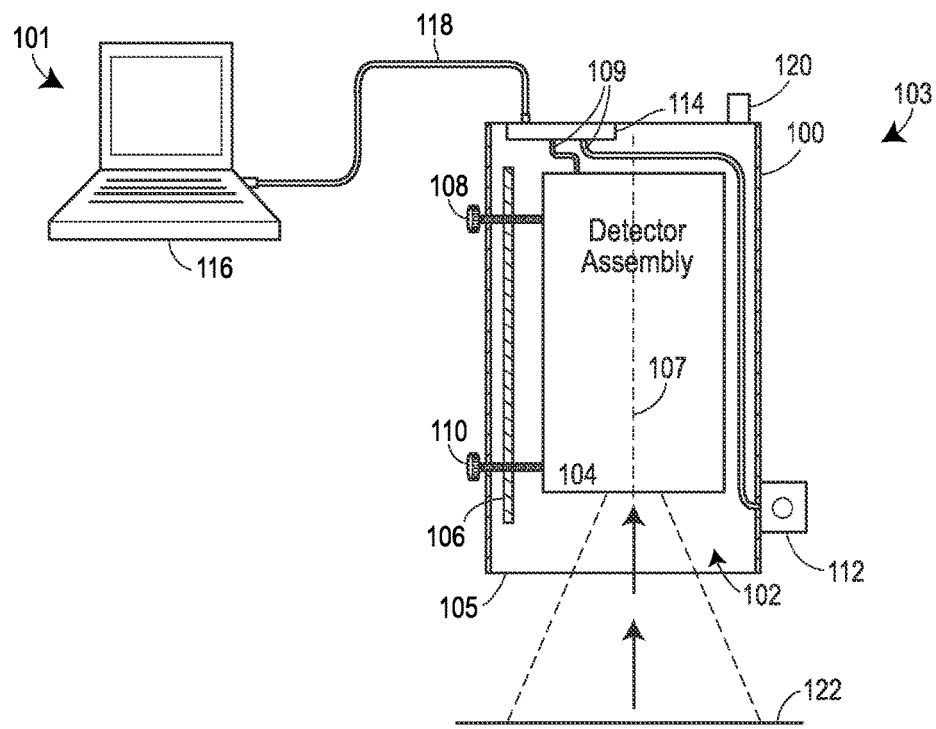
FIG. 8 depicts an example portable and modular NIR optical imager.

FIG. 8 depicts an embodiment of a hand-held, portable and modular NIR optical imager 101. A probe assembly 103 includes a probe body 100 formed as a hollow housing that contains a face 105 with an opening 102. The probe body 100 has a small size (around 67×76×120 mm, in one embodiment) such that it can be easily held in the hand of an operator. Light may enter the probe body 100 of the probe assembly 103 through the opening 102 and propagate into a detector assembly 104. The detector assembly 104 may be mounted on the interior of the probe body 100 by means of one or more rails 106, and the detector assembly 104 may move along the rail 106 along an optical axis 107 of the detector assembly 104 to adjust the detection area of the detector assembly 104. The detector assembly 104 may be held in position along the rail 106 by one or more pieces of fastening hardware, such as bolts 108 and 110 to maintain a fixed distance from the subject tissue and, accordingly, maintain the desired detection area. A source attachment point 112 is disposed on a side of the probe body 100 for attaching a light source assembly (not shown in FIG. 8). While the source attachment point 112 is disposed on one side of the probe body 100, toward the opening 102, it should be apparent that the source attachment point 112 may be placed at any convenient position on the probe body 100, including on the top surface. Additionally, while only one source attachment point 112 is depicted and described, multiple source attachment points 112 may be included. Where multiple source attachment points 112 are included, they may each be adapted to accept different light source assemblies, or may be adapted to accept similar light source assemblies. Additionally, multiple source attachment points (and the light source assemblies attached to each) may be individually controllable, and may be used simultaneously, sequentially, or individually.

In any event, both the source attachment point 112 and the detector assembly 104 are connected via one or more wires 109 to a communication and power module 114. The communication and power module 114 is connected to a computing device 116 by a cable 118. The computing device 116 may consist of a laptop or tablet computer, for example, and the cable 118 may consist of a Universal Serial Bus (USB) cable, for example. A tracking target 120 is mounted on the probe body 100 in various embodiments.

In the implementation depicted in FIG. 8, the computing device 116 (connected to the probe assembly 103 via the connection 118) provides control signals, provides power to the module 114, the detector assembly 104, and the source attachment point 112, receives control signals from the module 114 and/or the detector assembly 104 and the source attachment point 112, and collects data from the detector assembly 104. While the use of USB power and control allows for a small portable device that is not dependent on bulky control and power boxes, any suitable physical and/or logical interfaces may be used to provide control, power, and data communication to and/or from the computing device 116. For even more portability, other embodiments of the optical imager 101 may use a power storage unit, such as a battery (not shown), mounted in the probe assembly 103 for power and a wireless receiver (not shown) for control communication and data collection.

As described above, the detector assembly 104 is operable to move along the rail 106 such that the detection area at a tissue surface 122 is adjusted. That is, a smaller detection area results from the detector assembly 104 being positioned closer to the tissue surface 122, and a larger detection area may result from the detector assembly 104 being positioned further from the tissue surface 122. As will be appreciated, in some instances, adjusting the position of the detector assembly 104 may assist in focusing the image detected by the detector assembly 104. Once the operator determines a detection area, the detector assembly 104 may be fixed at a single location along the rail 106 by the bolts 108 and 110. The operator may adjust the bolts 108 and 110 and the position of the detector assembly 104 from the exterior of the probe body 100. Alternatively, in some embodiments, powered actuators (not shown) may move the detector assembly along the rail 106. In an example, these powered actuators are controlled via a wired or wireless connection to a laptop or tablet computer (e.g., the computing device 116), for example via the module 114, thus automating the adjustment of the detection area (or focusing the device). It is not required that the powered actuators be controlled by the computing device 116, though; instead, the powered actuators may be controlled by one or more controls (e.g., buttons, sliders, etc.) on the probe body 100. In any event, in such an automated implementation, the adjustment of the detection area may also be automatic to satisfy requirements of software or to optimize performance and increase ease of use.

In other embodiments, the detector assembly 104 may not be mounted on the rail 106. Instead, the detector assembly 104 may include exterior threads (not shown) operable to threadably engage corresponding threads on the interior of the probe body 100 or, alternatively, on the interior of an intermediary body (not shown) between the detector assembly 104 and the probe body 100, such that rotating the detector assembly 104 relative to the probe body 100 (or the intermediary body) moves the detector assembly along the axis 107 to adjust position and/or focus.

The tracking target 120 allows the 3D position of the probe assembly 103 and, in particular, the data collected by the probe assembly 103, to be coregistered with the image data captured by the detector assembly 104. In various implementations, the tracking target 120 may comprise one or more light emitting diodes (LEDs) that are tracked by an external, stationary external tracking device (not shown). This external tracking device may be a portable tracker that is mounted on a stand, such as a camera tripod. In other implementations, the tracking target 120 may consist of an acoustic tracking target 120 and/or an electromagnetic target (if the remainder of the probe assembly 103 does not include metallic parts) and/or it may comprise various kinematic sensors such as a gyroscope, accelerometer, and compass. This may be particularly useful in applications where the available space or existing light conditions do not allow for optical tracking.

The exemplary optical imager 101 illustrated in FIG. 8 is modular and may function with a variety of fixed or movable light source assemblies. For example, the operator of the optical imager 101 may easily attach a light source assembly designed for reflectance measurements, or the operator may attach a light source assembly designed for adjacent or trans-illumination measurements. Moreover, different light source assemblies may include light sources of differing wavelengths, intensities, polarizations, etc. may be easily exchanged, and light source assemblies may include various optical elements (such as lenses, diffusers, collimators, filters, expanders, etc.,) allowing for extreme customization of the light source assembly to fit the particular needs and/or desires of the operator. Still further, light source assemblies according to the various embodiments described herein may include a single light source (e.g., a single LED) or a multiplicity of light sources (e.g., an array of LEDs). Where the light source assembly includes a single light source (or, in fact, multiple light sources), a light source operable to emit multiple wavelengths (individually or concurrently) may be used. Where the light source assembly includes more than one light source, the multiple light sources may be the same (i.e., to provide greater light intensity), may be different (i.e., may be different wavelength light sources), or may be a combination of same and different light sources. In this way, the imager 101 can access a wealth of optical data without sacrificing portability and convenience. The modular design also lets users expand the functionality over time or as needed in the clinical application.

While FIG. 8 depicts the exemplary optical imager 101 described above, the optical imager 101 may be modified in any of a variety of ways. For example, in an embodiment, the communication and power module 114 may not be incorporated within the probe assembly 103 of the optical imager 101 and, instead, may take the form of an external control module (not shown). The external control module may perform the same functions as the communication and control module 114 described above, including serving as a communication interface between the detector assembly 104 and the source attachment point 112, and the computing device 116. The external control module may also provide power to the detector assembly 104 and to the source attachment point 112.

In still other embodiments, either the external control module or the communication and power module 114 may also function as the computing device 116, eliminating the need for an external computer and providing sufficient control, command, and processing power to control the device and thereby providing additional portability and convenience to the operator. In one or more of these embodiments, a display may be included and, for example, integrated with the control box or the communication and power module 114 to compensate for the loss of the display that would otherwise have been included in the computing device 116.

As will be appreciated from the examples above, the power source may likewise be incorporated into the optical imager 101 in various manners. As described above, power for the optical imager 101 and its various components may be provided by the computing device 116, or by a battery located elsewhere. In some embodiments, the power source is incorporated in the communication and power module 114 as a battery or as a connection to a power main. Likewise, in some embodiments, a small, separate mainline power supply or a battery may be incorporated within or attached to the probe body 100 of the probe assembly 103.

The optical imager 101 may likewise, in various embodiments, incorporate a wireless interface. For example, in a particular embodiment, the probe assembly 103 includes the communication and power module 114. The communication and power module 114 may include a battery for providing power to the remainder of the optical imager 101, or may include a coupling mechanism for coupling the communication and power module 114 to a separate power source (e.g., to an external battery, to a power main, etc.). In such embodiments, the communication and power module 114 may include a wireless interface for communicatively coupling the optical imager 101 to an external computer (not shown). The wireless interface may be any interface appropriate for the purpose including, by way of example and without limitation, Bluetooth®, IEEE 802.11a/b/g/n/ac, mobile telephony, etc. In any event, the external computer to which the optical imager 101 is coupled may serve as a control computer, or may merely be used to receive data wirelessly from the optical imager 101 after the diagnostic imaging is complete. In fact, there is no reason why any embodiment of the optical imager 101 or the probe assembly 103 specifically could not include a wireless communication interface for connecting to an external computer, the computing device 116, or any other device (e.g., remote storage, cloud storage, other diagnostic devices, etc.).

Figure 9A:
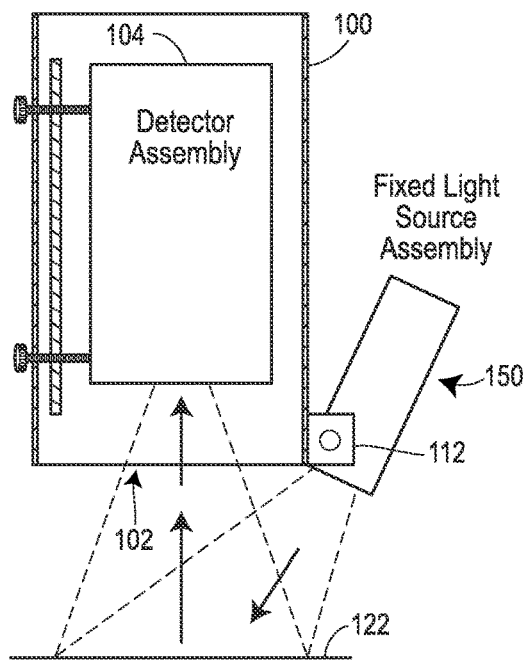
FIG. 9A depicts an example implementation of a probe assembly including a fixed light source assembly.

FIG. 9A illustrates an example implementation of a fixed light source assembly 150 designed for reflectance imaging. The fixed light source assembly 150 is attached to the probe body 100, as depicted in FIG. 8, at the source attachment point 112. The probe body 100 houses the adjustable detector assembly 104. The light propagating from the fixed light source assembly 150 is projected on the target tissue surface 122 and, after being scattered and/or attenuated in the target tissue surface 122, is reflected towards the detector assembly 104. The reflected light passes through the opening 203 and into the detector assembly 104. The attached fixed light source assembly 150 is not capable of trans-illumination imaging, but it may allow for slight adjustments of the light source assembly 150. For example, the source attachment point 112, may comprise a bolt or pin that allows the light source assembly 150 to pivot. A ring or collar (not shown) on the body, to which the attachment point 112 is coupled, may allow the light source assembly 150 to rotate around the probe body 100 and the detector assembly 104. The operator of the device may thus pivot and/or rotate the fixed light source assembly 150 to modify the angle at which the light is incident on the tissue surface 122.

Figure 9B:
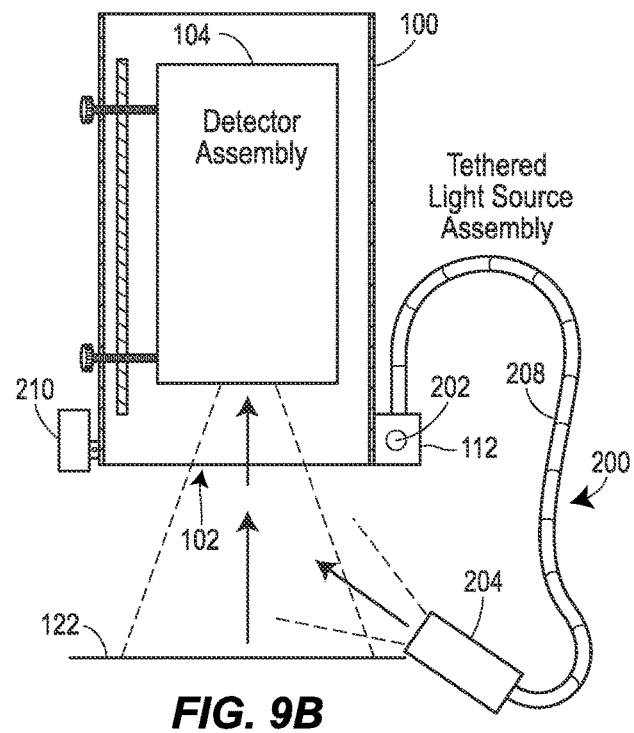
FIG. 9B depicts an example implementation of a probe assembly including a tethered light source assembly.

FIG. 9B illustrates an example implementation of a tethered light source assembly 200 designed for reflectance, adjacent, or trans-illumination imaging. The tethered light source assembly 200 is attached to the probe body 100 at the source attachment point 112. A flexible piping 208 extends between a coupling end 202 that connects the light source assembly 200 to the probe body 100 at the attachment point 112 and a light source module 204 that includes a light source and any optical components. The flexible piping 208 (which is not intended to be limited to any particular structure) is such that the light source assembly 200 may be positioned for reflectance, adjacent, or trans-illumination imaging. In some embodiments, the flexible piping 208 may be semi-rigid such that the light source assembly 200 and, in particular, the light source module 204, is moveable but remains in a desired position when placed in the position. The semi-rigid design frees the operator's hand that would, otherwise, necessarily have to hold the light source module 204 in place during imaging. Alternatively, the flexible piping 208 may be flexible enough that it does not maintain its position, which may facilitate maximum flexibility and/or positionability. As yet another alternative, the flexible piping 208 may be a segmented piping, such as the widely available ball-and-socket type coolant pipe.

In any event, the probe body 100 may include an anchor point 210 (in addition to the source attachment point 112) operable to receive the light source module 204. The anchor point 210 may provide a resting position for the light source module 204 when it is not in use. Additionally, in some embodiments, the anchor point 210 may be coupled to the probe body 100 by a pin and/or ring (as described above with respect to FIG. 9A) that may allow the light source module 204 to pivot and/or rotate, respectively, when the light source module 204 is placed in the anchor point 210. In this manner, the light source assembly 200 may operate as in a manner similar as the light source assembly 150 when the light source module 204 is placed in the anchor point 210.

The flexible piping 208 may contain wires which may couple the light source module 204 to the communication and power module 114. The wires may provide power to the light source module 204 and/or may provide communication of control and data signals between the communication and power module 114 and the light source module 204. The control and data signals may include, by way of example and without limitation: information about components (e.g., the light source and other optical components) in the light source module 204; control signals for controlling the components in the light source module 204; feedback signals from the light source module 204; and the like. In some embodiments, the light source assembly 200 may be powered by a self-contained power supply module, such as one containing batteries, and control of the light source assembly 200 may be maintained via a wired or wireless connection to the communication and power module 114 and/or the computing device 116.

Figure 9C:
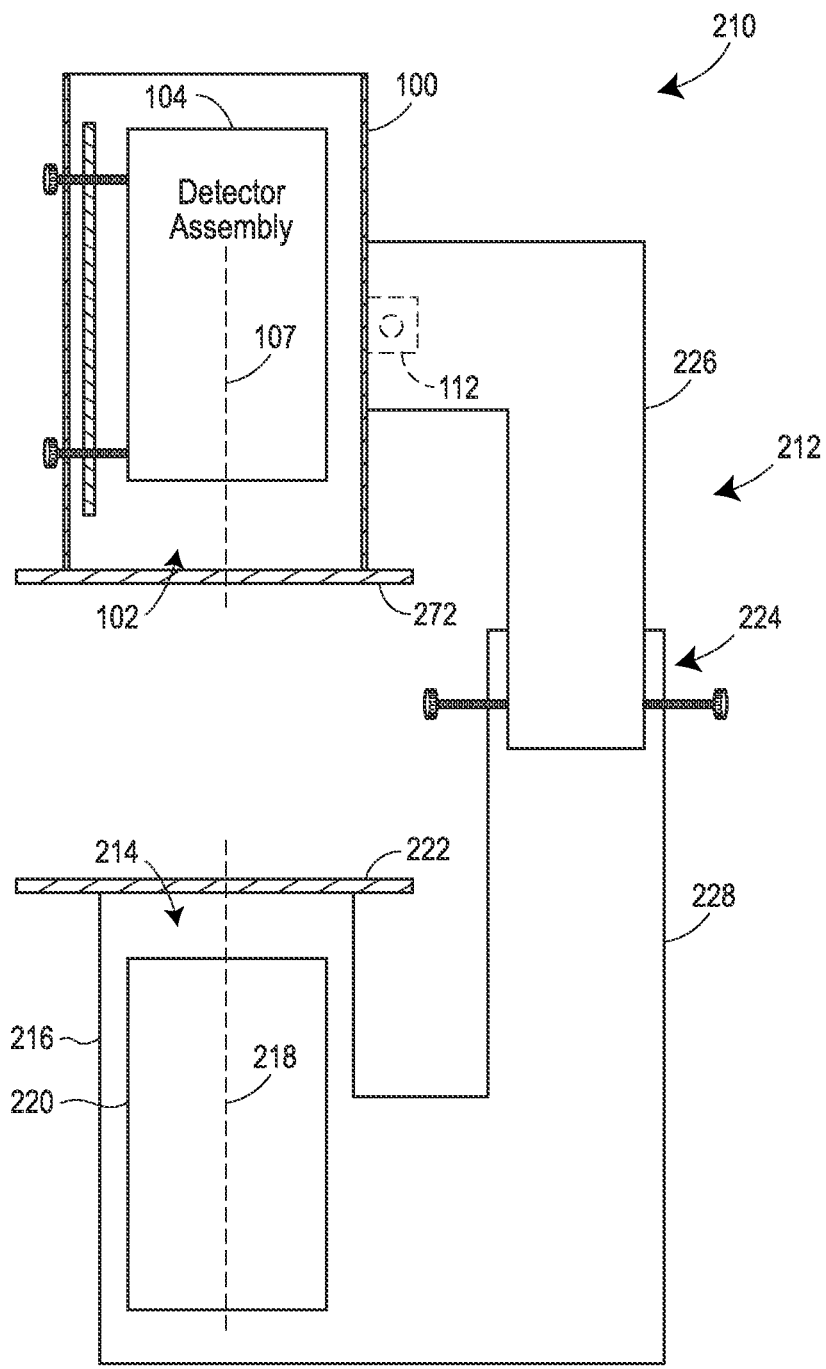
FIG. 9C depicts an alternative implementation of a probe assembly including a fixed light source assembly.

In other embodiments, a fixed light source assembly may be configured for trans-illumination using compression of the subject tissue. FIG. 9C depicts one such embodiment. In FIG. 9C, a probe assembly 210 may include generally, the probe body 100 of any of the previously described embodiments, including the detector assembly 104 in any embodiment described above, and including a transparent solid plate 272 (e.g., glass or plexiglass) that is transparent to the wavelength(s) of light to be detected and covers the opening 102. The probe body 100 may be physically coupled to an adjustable handle assembly 212. The adjustable handle assembly 212 may be handle-shaped in that it may be designed to be held easily in an operator's hand. The shape of the handle assembly 212 is designed such that the covered opening 102 of the probe assembly 100 is generally parallel to an opening 214 through which light from a source assembly 216 is output. That is, the optical axis 107 of the detector assembly 104 is generally aligned with an optical axis 218 of a source module 220 in the source assembly 216. The source module 220 may be any embodiment of the source module generally described above.

Like the detector assembly 104, the source assembly 216 also includes a transparent solid plate 222 (e.g., glass or plexiglass) that is transparent to the wavelength(s) of light to be detected and covers the opening 214. The plates 222 and 272 may be approximately the same size, and may be larger than either of the corresponding openings 214 and 102, respectively, such that they are able to compress the subject tissue between them.

The handle assembly 212 may have an adjustment mechanism 224 that facilitates adjustment of a detector portion 226 of the handle assembly 212 and a source portion 228 of the handle assembly 212 such that the probe body 100 and the source assembly 216 are movable to be closer to or further from one another, and to compress subject tissue (e.g., breast tissue) between the two for trans-illumination imaging. In the embodiment depicted in FIG. 9C, the detector portion 226 and the source portion 228 cooperate to create a telescoping mechanism that may be adjusted, for example, by turning a knob or, as another example, by depressing a release plunger to allow one portion to slide into and out of the other. While the handle assembly 212 is depicted in FIG. 9C as having squared off corners, in other embodiments, the handle assembly 212 may be completely rounded.

In some embodiments, the handle assembly 212 is modular and detachable from the probe body 100 connecting to the probe body 100, for example, at the source attachment point 212.

Figure 10A:
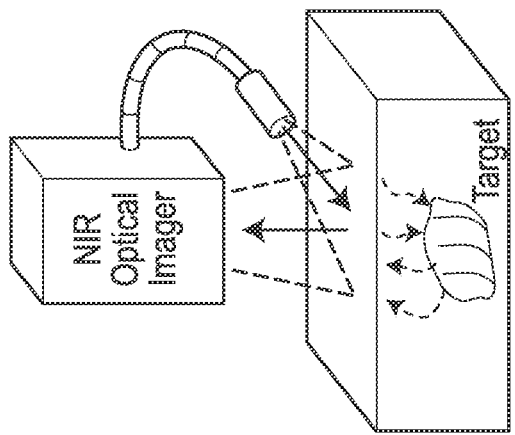
FIG. 10 depicts example applications of the optical imager for reflectance, adjacent, and trans-illumination imaging.
Figure 10B:
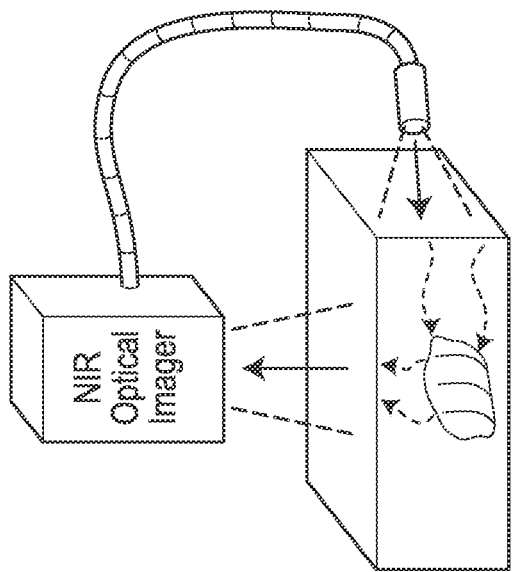
Figure 10C:
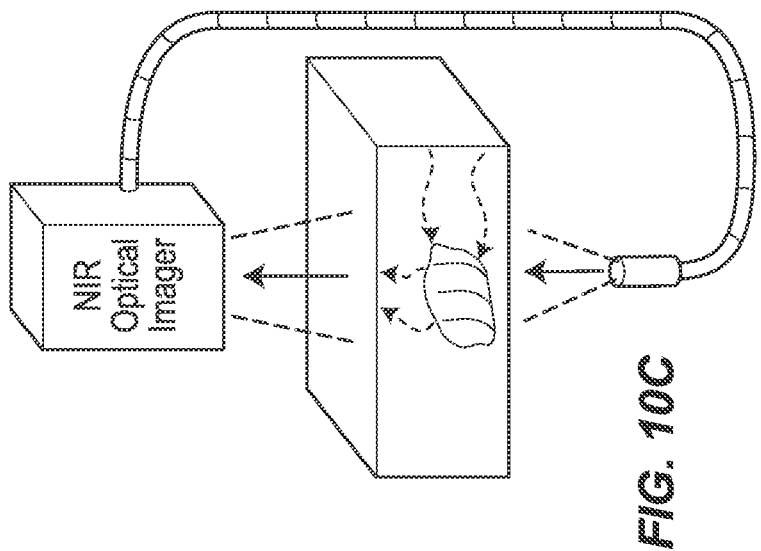

FIGS. 10A, 10B, and 10C illustrate example applications of the modular optical imager 101 with the light source assembly 200, for reflection, adjacent, and trans-illumination imaging, respectively. The ability to use the currently disclosed imager with a variety of imaging techniques is a great advantage compared with existing hand-held and, in particular, fiber-free hand-held, imagers that are limited to reflection or trans-illumination individually. As such, operating costs can be reduced by the need for only one simple and modular imager as compared with multiple imagers for multiple applications. In addition, the ability to use a single, portable device to perform both trans-illumination and reflectance imaging is preferable over carrying a multiplicity of different devices to achieve the same flexibility.

Example fixed and tethered light source assembly attachments 150 and 200 have been illustrated in FIGS. 9A and 9B, but other modular attachments or combinations of modular attachments may be used along with the probe body 100. For example, a combination of the fixed light source assembly 150 and the tethered light source assembly 200 may be implemented for illuminating the target from multiple directions simultaneously. Alternatively, two light source assembly attachments that operate at differing wavelengths may be implemented to obtain a greater range of optical data, as well as physiologically meaningful data such as oxy-hemoglobin (HbO), deoxy-hemoglobin (HbR), and total hemoglobin (HbT). A single probe assembly may be acquired for a clinical application with only the needed modular attachments, and other attachments may be acquired over time or as needed.

Detector Assembly and System

Figure 11A:
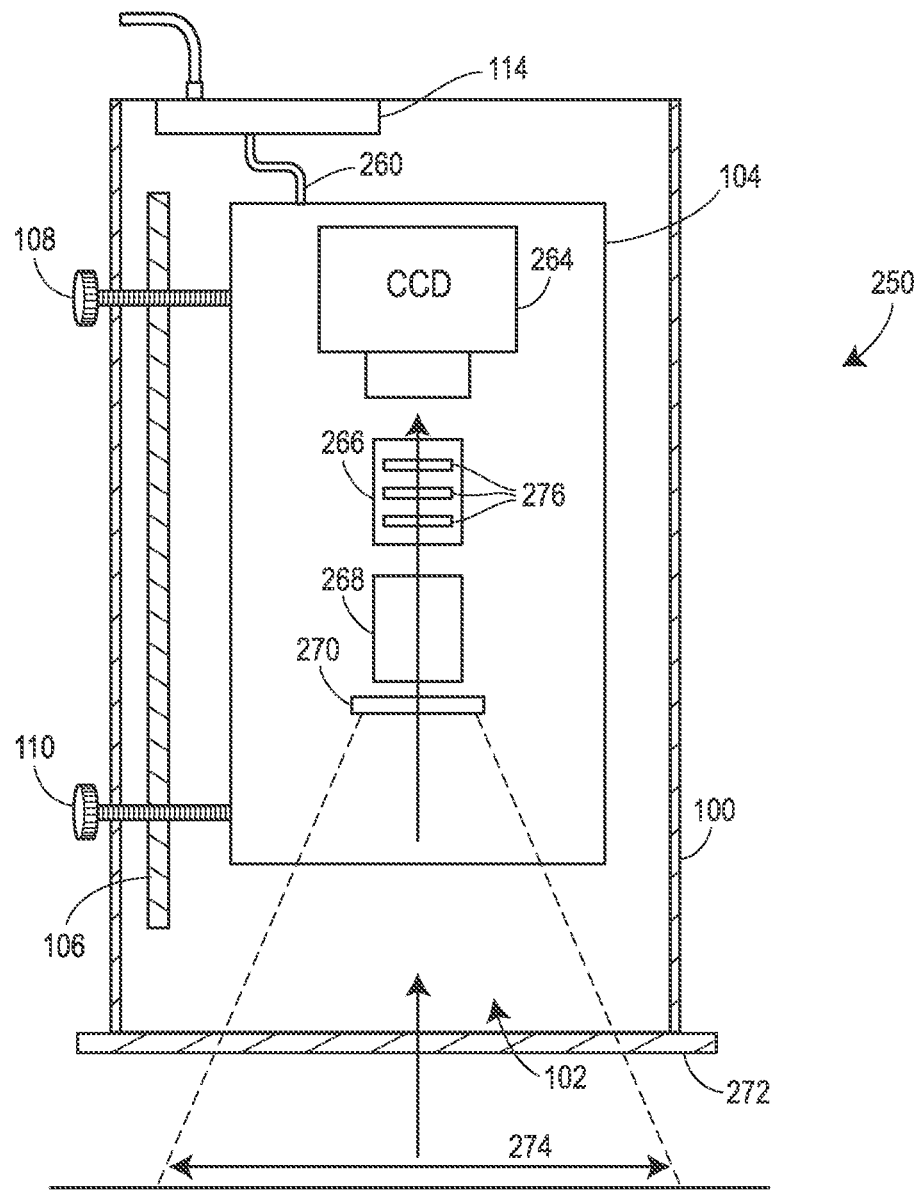
FIG. 11A depicts an example detector assembly.

FIG. 11A depicts an exemplary implementation of a probe assembly 250 illustrating the components of the detector assembly 104. In the probe assembly 250 the detector assembly 104 is mounted inside the probe body 100 on the rail 106. The detector assembly 104 is movable along the rail 106 and may be held stationary by the bolts 108 and 110. The detector assembly 104 is communicatively coupled via one or more wires 260 carrying signals to and/or from the communication and power module 114. In the probe assembly 250, the detector assembly 104 includes a charge-coupled device (CCD) 264, and may include a lens assembly 266, a focusing lens 268, and/or an optical filter 270. Light enters the probe body 100 through the opening 102 and then enters the detector assembly 104. The light entering the detector assembly 104 passes through the optical filter 270, the focusing lens 268, the lens assembly 266, and falls incident upon the CCD 264. In some embodiments, the opening 102 may be covered with a solid plate 272 (e.g., glass or plexiglass) that is transparent to the wavelength(s) of light to be detected. The transparent solid plate 272 may be useful when a flattened tissue surface is desired for imaging.

The CCD 264 is optimal for detecting with high resolution reflected, adjacent, or trans-illuminated light over an area 274. As will be readily appreciated, moving the detector assembly 104 along the rail 106 will adjust the detection area 274, making it smaller or larger as the detector assembly 104 is moved, respectively, toward or away from the subject tissue. Existing fiber-based imaging systems have a limited spatial resolution (owing to the fact that each detection fiber is a point detector) and become more complicated and expensive as the number of fibers increases to increase resolution. By using a CCD to directly image the tissue surface, the complexity, size, and cost associated with the optical fibers and the attendant equipment is eliminated. Moreover, in contrast to devices employing fiber-optic point detection, the presently described device is not only more portable, but useful for a variety of applications for which previous imaging devices were not useful, including: field applications, non-contact imaging applications, and the like.

The exemplary CCD 264 captures images with high NIR sensitivity, high spatial resolution (752×582 pixels, for example), and a high frame rate (30 frames per second, for example). Other CCDs or devices substituted for the CCD 264 may have other properties according to the desire of the user, and the modular design of the imager 101 provides swapability (i.e., the ability to quickly exchange one component for another) to allow for replacement of a damaged component or exchange of one component for another. Data corresponding to the image detected by the CCD 264 are transferred, via the wires 260, through a connector (which may be housed in the communication and power module 114) to a low-cost frame grabber. The frame grabber may be part of the communication and power module 114 or it may be part of the computing device 116. In any event, the frame grabber converts the analog image signal output from the CCD 264 into digital data, for example, by implementing, among other things, an analog to digital converter (ADC). The digital data may then be processed by one or more hardware and/or software modules on the computing device 116. Alternatively, the CCD 264 may include an on-board frame grabber. In such an embodiment, the data from the CCD 264 may be directly processed in the computing device 116.

Referring still to FIG. 11A, the lens assembly 266 contains one or more lenses 276. The lenses 276 may be replaced or exchanged depending on the clinical application. In some implementations, the lenses 276 include a combination of converging and diverging lenses such that a focused image of the detected area 274 is formed on the CCD 264. In other implementations, the lenses 276 include a combination of converging and diverging lenses such that the image of the detected area 274 is magnified. The software that analyzes the data from the detector assembly 104 may be optimized for a certain image orientation and/or magnification, and the lenses 276 in the lens assembly 266 may be used to provide the software with the expected types of data.

In addition to the light propagating through the lens assembly 266 and onto the CCD 264, the light may pass through the focusing lens 268 and/or the optical filter 270. The focusing lens 268 focuses the raw light that is reflected by or transmitted through the target tissue. The light entering the detector assembly 104 may be very diffuse and/or very attenuated. The focusing lens 268 gathers this light and guides it into the other optical elements (such as the lens assembly 266) of the detector assembly 104. The optical filter 270 conditions the light such that the CCD 264 and software can appropriately process the signal. For example, absorptive filters may only pass light of a certain wavelengths and other filters may align the polarization of the incident light. Using such a filter, radiation that might cause the CCD 264 to malfunction can be eliminated and interfering signals (such as the signal from the NIR source) can be removed, or such a filter might allow the for specialized analysis. In some embodiments, multiple filters may be used to fine tune the properties of light incident on the CCD 264, such as by separating the emission signal from the attenuated excitation signal, or attenuating a high intensity detected signal.

Of course, the optical elements 266-270 need not be arranged in the order depicted in FIG. 11A and described above. In some embodiments, for example, the focusing lens 268 may be optically adjacent (i.e., the first element from)

the CCD 264. In other embodiments, the focusing lens 268 may be an integral part of the CCD 264 (e.g., when the CCD 264 is a camera assembly).

Figure 11B:
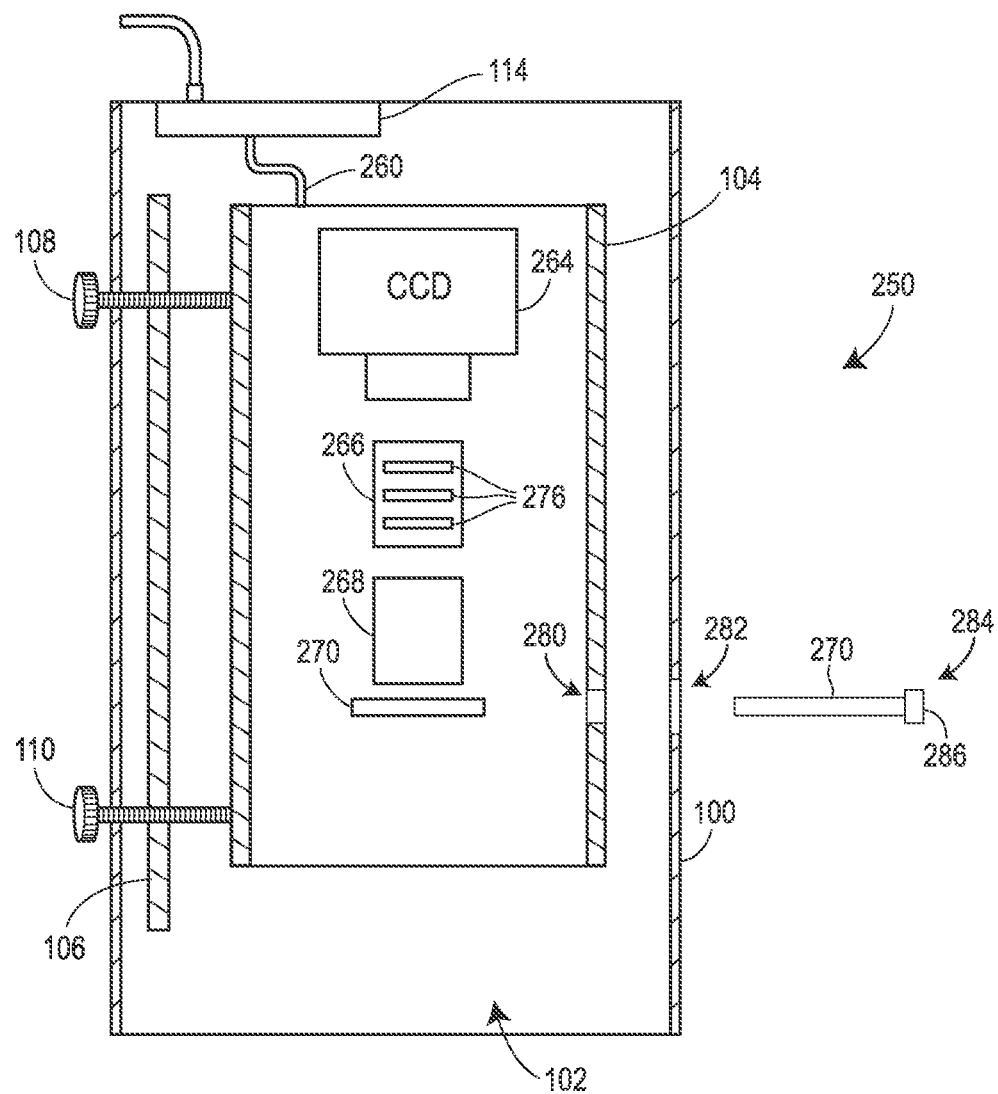
FIG. 11B is a side view of an example detector assembly depicting a particular aspect of the assembly.

Referring now to FIG. 11B, a particular optional aspect of the imager 101 is depicted. Specifically, in some embodiments, a slot 280 in the side of the detector assembly 104 and/or a slot 282 in the probe body 100 allows the operator of the optical imager 101 to add or exchange optical elements, including in various embodiments, the CCD 264, the lens assembly 266, the filters 276, and/or the focusing lens 268. That is, the operator may be able to add or exchange a component without disassembling the probe body 100 (through the slot 282 in the probe body). If the component in question is within the detector assembly 104, a corresponding slot 280 in the detector assembly 104 may allow the operator to add or exchange the component in the detector assembly 104. In some embodiments, each replaceable/exchangeable component has a slot 280 in the detector assembly 104, and the detector assembly 104 may be moved within the probe body 100 such that the slot 280 for each particular component may be aligned with the slot 282 in the probe body 100. In still other embodiments, one or more of the components may be part of a component cartridge 284 that may pass through the slot 282 and into the slot 280 such that an integrated slot cover 286 covers or fills the slot 280, blocking external light from entering the detector assembly 104.

The ability to add or exchange optical elements accommodates various imaging modalities without the need to disassemble the probe body 100 and/or the detector assembly 104 or purchase a separate detector assembly. In addition, access to the optical elements through the slots 280, 282 opens the possibility of imaging with a variety of imaging modalities in quick succession, thus reducing the necessary time for some exams.

In some embodiments, an additional slot (not shown) in the side of the probe body 100 and/or in the side of the detector assembly 104 allows the operator to perform manual focusing of the image on the CCD 264.

In contrast to fiber-based detectors, the detector assembly 104 depicted in FIG. 11A can operate with or without contacting the target tissue. The probe body 100, and thus the detector assembly 104, can be moved by hand towards or away from the tissue surface 122. This flexibility of use has unique advantages. First, the detected area 274 and/or focus of the CCD 264 may be adjusted in real-time by moving the probe body 100 closer to or further from the tissue surface 122 (in addition to adjustments made by moving the detector assembly 104 along the rail 106). Second, the disclosed imager 101 may be used in surgical setting, or in any setting in which inflamed or wounded tissue is present, where making contact with tissue is not an option. As such, the imager 101 may be used for pre-operative, intra-operative, and post-operative imaging applications without the need to modify the imager 101 or purchase specialized imaging systems.

Light Source Assembly and System

Figure 12:
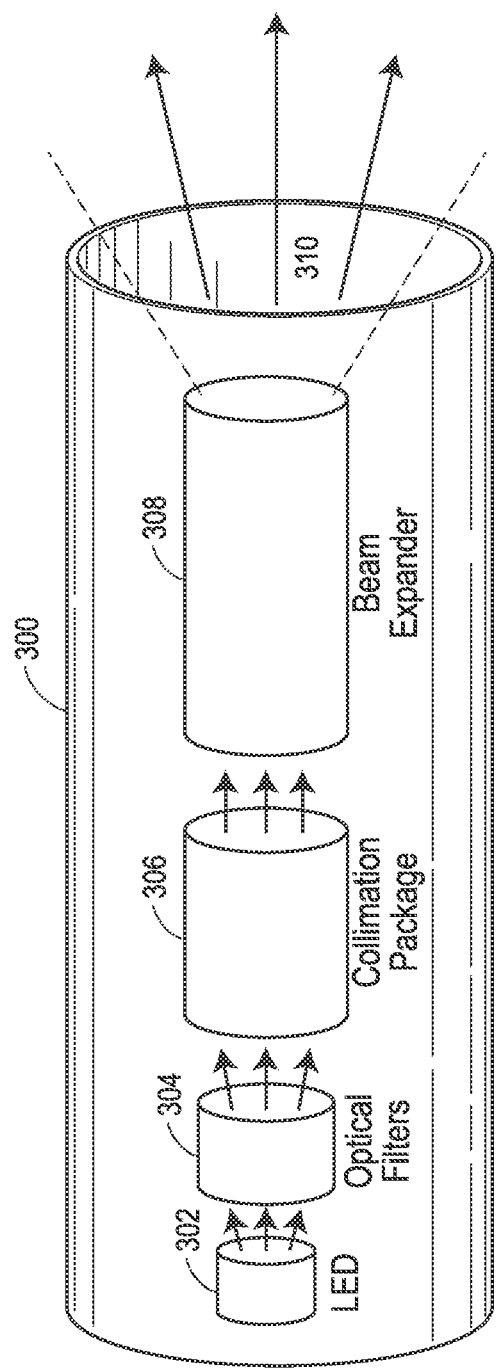
FIG. 12 depicts an example light source assembly.

FIG. 12 illustrates an embodiment of a light source module 300, which may be included in or as the light source assembly 150 in FIG. 9A or may be included as the light source module 204 in FIG. 9B. The light source module 300 may be fixedly or semi-rigidly attached to the probe body 100, as depicted in, for example, FIG. 9A. Alternatively, the light source module 300 may be coupled to the probe body 100 as the light source module 204 of the light source assembly 200 in FIG. 9B. The light source module 300 includes a light source 302, and may additionally include one or more of: optical filters 304, a collimation package 306, and a beam expander 308. The light emitted by the light source 302 propagates through the optical filters 304, the collimation package 306, and the beam expander 308 before exiting the light source module 300 via an opening 310. In FIG. 12, the light source 302 is depicted as an LED and, accordingly, the present description describes the light source 302 in terms of an LED. However, it should be understood that other light sources may be substituted for the LED in various embodiments of the claimed methods and apparatus.

In an embodiment, the light source 302 is an LED providing NIR light having a wavelength of 700-900 nm. In another embodiment, the light source 302 is an LED providing NIR having a wavelength between 650 and 1000 nm. As described above, the light source 302 may be a single LED, multiple LEDs, an array of LEDs, etc. Multiple LEDs may be a single wavelength or multiple wavelengths. The LED may be driven by a driver circuit operable to control the current flow. For example, current flow to the light source 302 may be driven between 0 and 200 mA in one embodiment, using a variable resistor. For some applications an alternate light source may be preferred. In some embodiments, for example, the light source 302 in the light source module 300 may be modular to allow other light sources, for example a laser source, to be exchanged for the present source (e.g., the LED) without exchanging or disturbing other optical elements (e.g., the filters, collimation package, and beam expander). In other embodiments, the operator may exchange the entire light source assembly, such as the light source module 300, for a different light source assembly that includes a different light source (laser, etc). The operator may also choose to image a single target with a variety of light sources.

In a manner similar to the detector assembly 104, the light source module 300 may be mounted on a rail within (or threadably engaged with) the light source assembly 150, such that the area upon which the light is incident may be adjusted by moving the LED 302 closer to or further from the target tissue surface.

The light source module 300 may be physically and communicatively coupled to the computing device 116 and, in some embodiments, is coupled to the computing device 116 through the communication and power module 114. Of course, functionality of the computing device 116 and/or the communication and power module 114 may be included in a single on-board module (e.g., in the module 114) or in an external control box. Control of the light source module 300 (and detector assembly 104) by the computing device 116 allows the probe assembly 103 to maintain, at most, only one external connection. With a minimal number of external connections, the probe assembly 103 is easy to maneuver, especially in clinical applications where space is restricted. Alternatively, the light source module 300 may operate via a driver circuit (not shown) using a variable resistor to control current flow. This driver circuit may be housed in the control box or inside the probe body 100.

In the embodiment depicted in FIG. 12, light emitted from the source 302 passes through the optical filters 304. The optical filters 304 may comprise absorptive or polarizing filters similar to those discussed in reference to the detector assembly 104. In addition, a diffusing filter may scatter or "soften" the light incident from the source 302. The collimation package 306 may fully or partially align the direction of propagation of light exiting the optical filters 304. The beam expander 308 expands the cross-sectional area of the beam of light exiting the collimation package 306 to a predefined width. In one implementation, the beam expander 308 and collimation package 306 are adjustable such that the beam width and amount of collimation can be adjusted before, during, and/or after imaging. This adjustment may be a manual internal adjustment or may be performed automatically according to an external control signal received from the communication and power module 114 or the computing device 116. One or more signals may originate at the light source module 300 indicating to the communication and power module 114 and/or the computing device 116 the precise components included in the optical path of the light source module 300. Signals originating at the light source module 300 may also include feedback signals from the components of the light source module 300 or from components not previously described. For example, in an embodiment, the light source module 300 includes one or more light sensors (not shown) that detect light emitted by one or more of the components, and provides feedback to the communication and power module 114 and/or the computing device 116. In an embodiment, an optical power meter (e.g., the PM 100 from Thorlabs) with a silicon sensor (e.g., the S121B from Thorlabs) may validate the stability of the light source 302 and provide the feedback to the computing device 116.

Likewise, one or more control signals may originate at the computing device 116 and/or the communication and power module 114 to control the light source module 300 and its output. For example, exemplary control signals may allow perform any of the following tasks manually or automatically: providing to or withdrawing power from the light source 302, adjusting power to the light source 302, adjusting a controllable property of the optical filters 304 and/or the collimation package 306, adjusting the properties of the beam expander 308 to increase or decrease the beam width, and the like.

Figure 13:
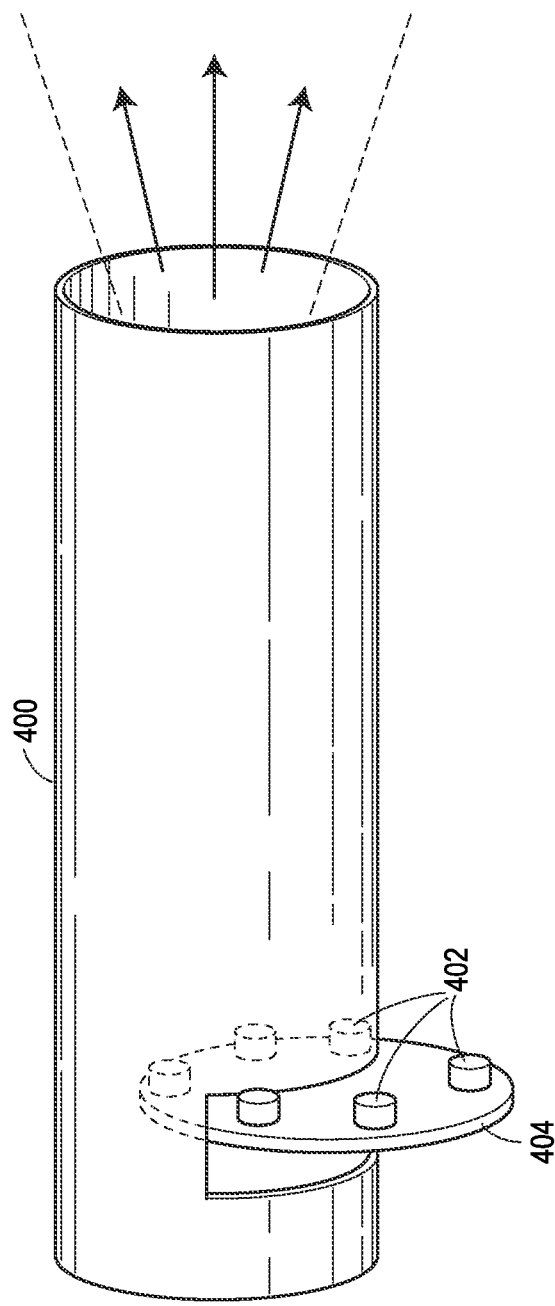
FIG. 13 depicts an example light source assembly with optical elements disposed on a rotary dial.

FIG. 13 illustrates a light source assembly 400 with one or more optical elements 402 on a rotary dial 404. In an embodiment, the optical elements 402 comprise a variety of light sources with differing wavelengths, including, in at least one embodiment, a white light source. By operating the rotary dial 404, different light sources may be placed into operation and, thereby, the operator of the optical imager 101 may easily change the wavelength of incident light. As will be appreciated, simple substitution of one light source for another to facilitate imaging at varying wavelengths is advantageous for various clinical applications, and because it eliminates the need to carry multiple wavelength light source modules or more than one imaging device. In various other embodiments, optical filters, beam expanders, and/or other optical elements may be disposed on rotary dials such that the elements are easily exchanged. Of course, similar arrangements may be used with the detector assembly 104 and, in particular, rotary dials may provide an easy means for exchanging light sources 264, lens assemblies 266, focusing lenses 268, and/or filters 270.

Similar to the detector assembly 104, the light source module 300 may be used in both contact or non-contact imaging applications. Moreover, if an tethered light source assembly, such as the tethered light source assembly 200, is employed, the operator may choose to use a combination of contact and non-contact imaging when appropriate. The detector assembly 104 may be placed in contact with the tissue surface while the light source module 300 is not in contact with tissue surface, or the light source module 300 may be placed in contact with the tissue surface while the detector assembly 104 is not in contact with the tissue surface. This flexibility may be convenient when imaging hard to reach areas or when a patient in unable to optimally position herself.

Computer System and Implementation

Figure 14:
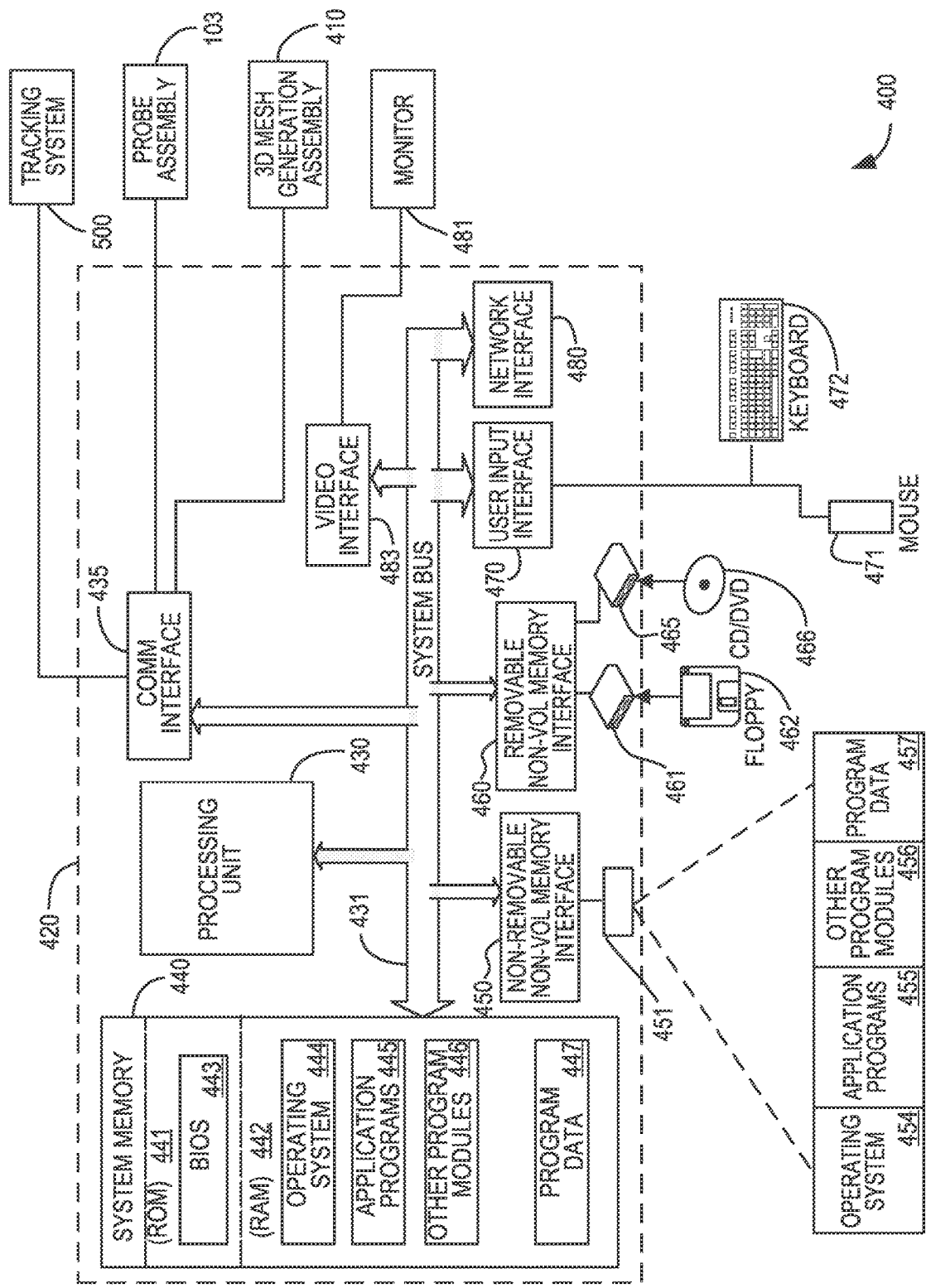
FIG. 14 is a block diagram of an imaging system in accordance with the presently described embodiments.

FIG. 14 is a block diagram depicting an embodiment 400 of a hand-held optical imager with 3D tracking facilities. FIG. 14 depicts a logical view of a computing device in the form of a computer 420 that may be used in such a system (e.g., as the computing device 116). For the sake of illustration, the computer 420 is used to illustrate the principles of the instant disclosure. However, such principles apply equally to other electronic devices having sufficient computing power, including, but not limited to, cellular telephones, smart phones, tablet computers, netbook computers, workstations, and personal digital assistants, to name a few. Components of the computer 420 may include, but are not limited to a processing unit 430, a system memory 440, and a system bus 431 that couples various system components including the system memory 440 to the processing unit 430. The system bus 431 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, front side bus, and Hypertransport™ bus, a variable width bus using a packet data protocol.

Computer 420 may include one or more serial, parallel, wireless, or other communication interfaces 435, such as Universal Serial Bus (USB) interfaces, IEEE-1394 (FireWire) interfaces, RS-232 interfaces, RS-423 interfaces, RS-485 interfaces, IEEE-488 (HPIB or GPIB) interfaces, mobile terrestrial interfaces, IEEE 802.11 interfaces, Bluetooth® interfaces, etc. The computer 420 may communicate through the communications interface 435 with, for example, the detector assembly 104, the light source module 300, a 3D mesh generation assembly 410, and/or a tracking system 500 (as described in detail below).

Computer 420 typically includes a variety of computer readable media. Computer readable media can be any available media that can be accessed by computer 420 and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 420.

The system memory 440 includes computer storage media in the form of volatile and/or nonvolatile memory such as read only memory (ROM) 441 and random access memory (RAM) 442. A basic input/output system 443 (BIOS), containing the basic routines that help to transfer information between elements within computer 420, such as during start-up, is typically stored in ROM 441. RAM 442 typically contains data and/or program modules that are immediately accessible to and/or presently being operated on by processing unit 430. By way of example, and not limitation, FIG. 14 illustrates operating system 444, application programs 445 (such as one or more modules embodying part or all of the methods described herein), other program modules 446 (such as one or more modules embodying part or all of the methods described herein), and program data 447. By way of example, the application programs 445 and the other program modules 446 may implement control of and/or cause the processor 430 to process data received from the detector assembly 104, the light source module 300, and the tracking system 500. For instance, with respect to the light source module 300, the programs 445 and modules 446 may implement control of the output power, etc. source 302. As another example, with respect to the detector assembly 104, the programs 445 and modules 446 may implement control of the CCD 264, the lens assembly 266, the filter assembly 268, the focusing lens 270, may active actuators for adjusting the position of the detector assembly 104 within the probe body 100, and/or may process data (e.g., image information received from the probe assembly 103) received from the CCD 264. As yet another example, with respect to the tracking system 500, the programs 445 and modules 446 may process data received from the tracking system 500 to determine current position and/or orientation data of the probes assembly 103 and/or of the subject of study, may process data received from the tracking system 500 and the CCD 264 to co-register image data and 3D mesh data, or may implement control of one or more aspects of the tracking system 500. As still another example, with respect to the 3D mesh generation assembly 410, the programs 445 and modules 446 may process data received from a 3D surface scanner (i.e., a scanner for generating a surface geometry or 3D mesh), may implement a control function of the 3D surface scanner, may implement control of a positioning device associated with the 3D surface scanner, etc.

The computer 420 may also include other removable/non-removable, volatile/nonvolatile computer storage media. By way of example only, FIG. 14 illustrates a hard disk drive 451 that reads from or writes to non-removable, nonvolatile magnetic media, a magnetic disk drive 461 that reads from or writes to a removable, nonvolatile magnetic disk 462, and an optical disk drive 465 that reads from or writes to a removable, nonvolatile optical disk 466 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 451 is typically connected to the system bus 431 through a non-removable memory interface such as interface 450, and magnetic disk drive 461 and optical disk drive 465 are typically connected to the system bus 431 by a removable memory interface, such as interface 460.

The drives and their associated computer storage media discussed above and illustrated in FIG. 14, provide storage of computer readable instructions, data structures, program modules, and other data for the computer 420. In FIG. 14, for example, hard disk drive 451 is illustrated as storing operating system 454, application programs 455, other program modules 456, and program data 457. Note that these components can either be the same as or different from operating system 444, application programs 445, other program modules 446, and program data 447. Operating system 454, application programs 455, other program modules 456, and program data 457 are given different numbers here to illustrate that, at a minimum, they are different copies. A user may enter commands and information into the computer 420 through input devices such as a keyboard 472 and pointing device 471, commonly referred to as a mouse, trackball, or touch pad. Other input devices (not shown) may include a microphone, joystick, game pad, satellite dish, scanner, digital camera, or the like. These and other input devices are often connected to the processing unit 430 through a user input interface 470 that is coupled to the system bus 431, but may be connected by other interface and bus structures, such as a parallel port, game port or a universal serial bus (USB). A monitor 481 or other type of display device is also connected to the system bus 431 via an interface, such as a video interface 483.

The computer 420 may operate in a networked environment using logical connections to one or more remote computers (not depicted) over a network interface 480, such as broadband Ethernet connection or other known network. The computer 420 may communicate via the network interface 480 with one or more other computers executing one or more software modules embodying a portion of the methods described herein, for example to split the processing requirements for real-time data manipulation among multiple computers.

3D Mesh Generation

In both modeling and image reconstruction, a region of interest(s) (e.g. 2-D or 3D tissue object or phantom) may be divided into discrete 2-D or 3D elements. Due to the limited detection area of the detector assembly 104, sensor data are captured only for a portion of the region of interest at one time. To obtain three-dimensional visualization of a large region of interest, each time the probe assembly 103 is moved, the position and orientation of the probe assembly 103 may be monitored and co-registered or mapped. As used herein, co-registration refers to the mapping of sensor data for a particular region onto to a map (e.g., a discretized mesh) of the entire region of interest(s). Generally, registration provides 3D location and orientation data for the sensor data. For example sensor data captured during a first period at a first position of the probe assembly 103 may be mapped to corresponding first positions of a map of the entire region of interest. To implement self-registration or co-registration of the sensor data for the region of interest, a tracking system may be used to monitor the location of the probe assembly 103.

Figure 15:
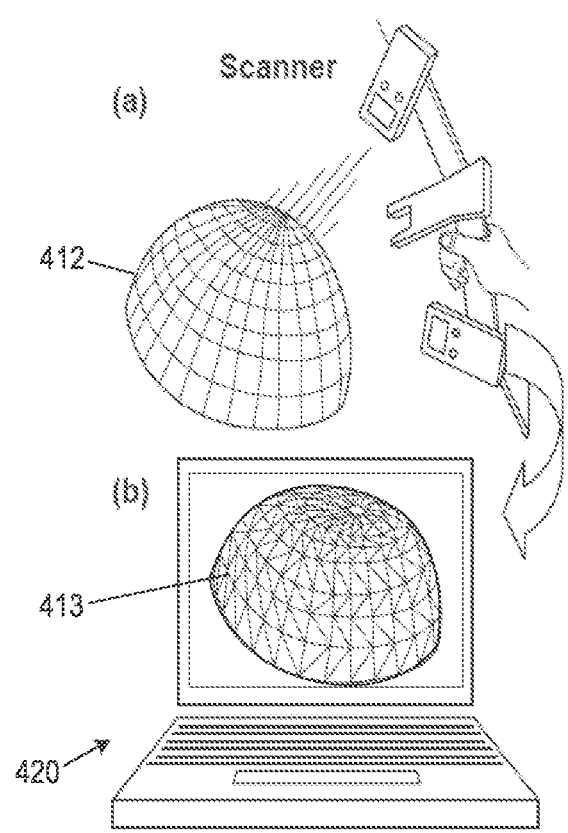
FIG. 15 depicts a scanning system for generating a 3D mesh.
Figure 16:
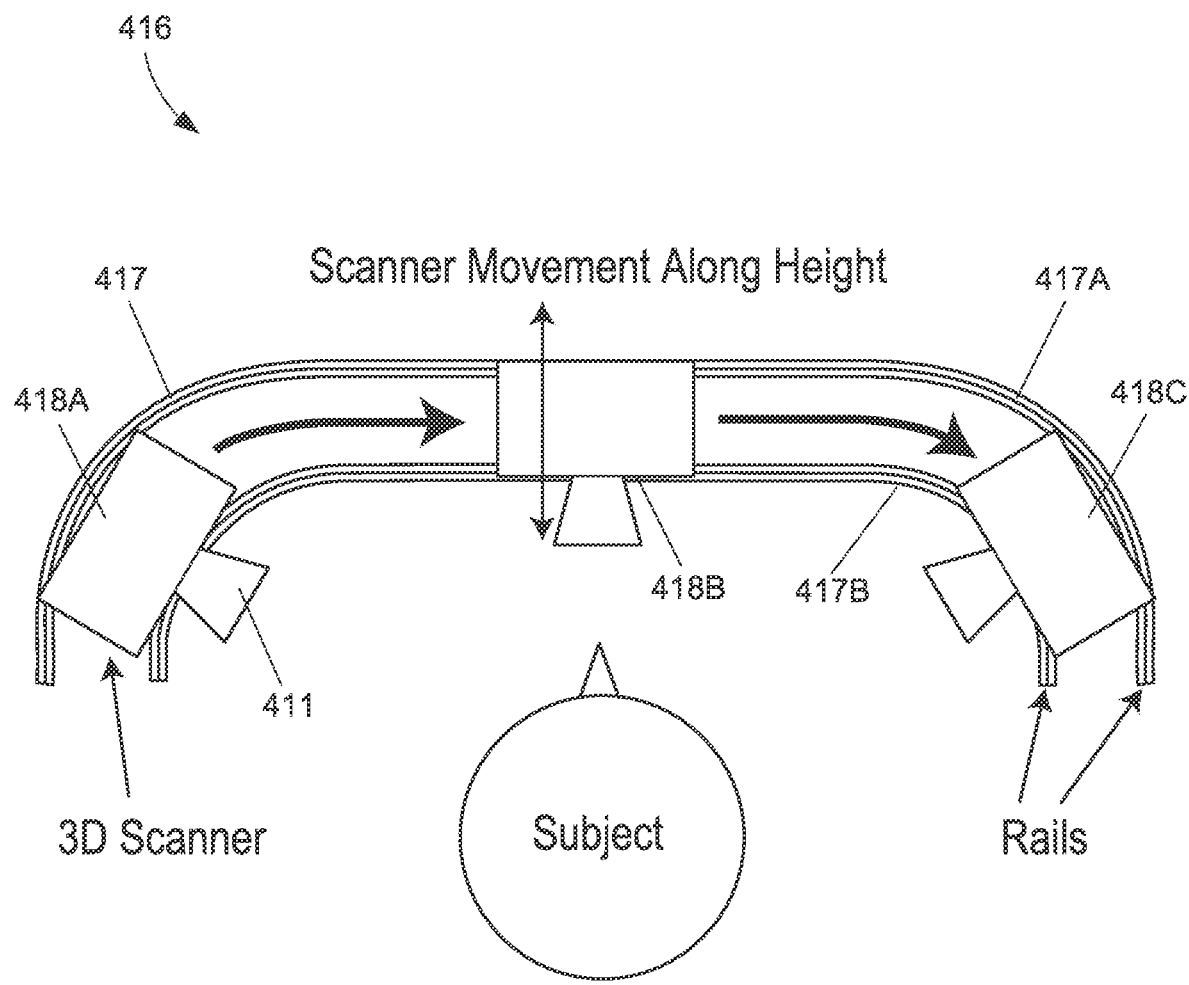
FIG. 16 illustrates an automatic component of a scanning system for generating a 3D mesh.

FIGS. 15 and 16 illustrate possible embodiments related to the obtaining 3D surface sensor data using a self-registering (automatic registering) hand-held probe based imaging system. FIGS. 15 and 16 relate particularly to a 3D mesh generation assembly 410. A three-dimensional optical scanner 411, as known in the art, may be used on a target object 412 (without any contact) to provide a 3D surface image of the target object 412, which can be volume rendered and discretized using appropriate meshing software, as known in the art. In some embodiments, the volume rendering process may involve generating a three-dimensional (3D) mesh 413 of point coordinates or point locations sub-surface to the rendered 3D surface image (e.g., for the entire volume of the target object 412). This 3D mesh may be known as a "phantom mesh" because it serves as a structure over which the target data may be mapped or overlaid or with which the target data may be co-registered (as described below).

While not depicted in the figures, it is also possible to capture 2D images (e.g., photographs) of the target object 412 from multiple angles, after which the photographs may be "stitched" together by software to create a phantom geometry and, eventually, the phantom mesh.

The 3D mesh 413 of the target object 412 may be displayed on the monitor 481 of the computing device 420. An imager 414 for collecting sensor data, such as the probe assembly 103 described above, may then be traced over the target object 412 to obtain sensor data. The 3D location map of the probe 414 with respect to the 3D mesh 413 of the target object 412 may be obtained using the tracking system 500 (described below). In some embodiments, the computing system 420 may be programmed (e.g., using appropriate software and algorithms, such as those described herein) to receive sensor data from the probes 414 for a time period, receive probe position data and/or orientation data from the tracking system 500 for the time period, and co-register the received data with appropriate mesh locations on the 3D mesh 413 based on the position data. In this manner, the location data and the sensor data collected over a region may be mapped to the corresponding region on the 3D mesh 413 surface to generate co-registered map sensor data 415. The computing device 420 may co-register or map sensor data with respect to a reference position arbitrarily (or specifically) chosen on the 3D mesh 413 of the target object 412. The computing system 420 may be further programmed to process the sensor data before and/or after mapping/co-registering to the mesh 413 depending on a particular application of the sensor data.

In some embodiments, the 3D mesh generation assembly 410 may include an automatic scanning mechanism 416, such as that illustrated in FIG. 16. The automatic scanning mechanism 416 includes a 3D surface scanner such as the 3D surface scanner 411 (or an image capture device) movably mounted on a positioning device 417. The positioning device 417 may be one or more rails (such as rails 417A, 417B depicted in FIG. 21) upon which the 3D surface scanner 411 may be mounted. A motor (not shown) on the optical scanner 411 or integrated with the rail(s) 417 may position and/or move the optical scanner 411 from an initial position 418A, around the subject to be imaged to a final position 418C, passing through intermediate positions such as a position 418B. The optical scanner 411 may scan the subject continuously or, at least, a plurality of times, as it moves from the initial position 418A to the final position 418C. The positioning device 417 is not limited to the rails depicted in FIG. 16, but instead may be a robotic arm, one or more cables, etc. In some embodiments, the movement of the optical scanner 411 via the positioning device 417 is controlled by the computing device 420. The positioning device 417 may scan the subject at each of a plurality of heights. For example, in one embodiment, the scanner 411 scans the subject by moving along the rails 417 at a first height, and then the height of the rails 417 (and the scanner 411 mounted thereon) is adjusted and the process repeated. This process may be iterated multiple times adjusting the height of the rails 417 each time by, for example, 0.5 inches, 1 inch, 3 inches, etc.

Probe Tracking

Some single-probe optical imaging systems have employed acoustic trackers, which may be commercially available, to track the position of the probe head while acquiring imaging data. As described in U.S. patent application Ser. No. 12/625,476, entitled "Hand-Held Optical Probe Based Imaging System with 3D Tracking Facilities," and incorporated herein in its entirety by reference, acoustic trackers that determine probe location via sound may be appropriate for an optical imaging system because acoustic receivers may be small, lightweight, and inexpensive. In some embodiments, two or more acoustic trackers could be used with the dual probe head design described herein. Additionally, in some embodiments, the tracking system 500 (see FIG. 19) may employ an optical tracking method and devices or an electromagnetic tracking method and devices, instead of an acoustic tracking method and devices.

Image Capture and Processing

The imager 101 may implement in software, in hardware, or in a combination of software and hardware, various modules operable to capture and process image data. In particular, a module may implement control of the detector assembly 104 and, more particularly, may implement control of the CCD 264. The camera control module may implement a video or image adaptor driver and the format can be searched and selected automatically.

A module may also be operable to implement image capture and processing. The image capture and processing module may provide one or more functions including, but not limited to: controlling preview mode, capturing images from the CCD 264, loading image data, loading color-map data, saving color-map data, editing color-map data, implementing median filtering (a non-linear spatial digital filtering technique), implementing histogram stretching and subtraction techniques. The latter allows the operator of the imager 101 to investigate the specific features of a measure NIR image by, for example, interrogating histogram density and/or extracting NIR intensity information for a region of interest to investigate a change in intensity.

A module may further be operable to record video. Each module may be stored in, and may store data in, one or more computer readable memories. The video recording module may be operable to provide real-time functional imaging, for example at frame rates of 30 frames per second and real-time subtracted imaging.

A module, which in certain embodiments is the image capture and processing module, is operable to perform 2D target localization based on histogram thresholding. A position of a detected target is estimated by using histogram thresholding techniques to distinguish between target and background based on histogram density. While thresholding techniques have been used previously, these thresholding techniques are normally used to distinguish a target if there is a distinct boundary in the histogram data. By contrast, NIR does not have this feature, since histograms or NIR image data generally exhibit a continuous slope change in intensity. To overcome this problem, a manually determined histogram threshold criteria is employed to detect the target position by using the predetermined threshold level, 5 percent, for example. From the subtracted image (between background image and target image), a histogram density is first calculated and the bottom 5 percent of histogram intensity is used as a threshold level for histogram thresholding. A target shape and its centroid position can be extracted using the histogram thresholding method. That is, if pixel value is under the threshold value, it is regarded as a target pixel and, therefore, as part of the target area.

Coregistration

Utilizing data provided by the modules described above, a co-registration module may be operable to perform coregistration. A three-dimensional scanner and appropriate meshing software may be used to render a three-dimensional map (e.g., a mesh of point locations) of the target three-dimensional tissue object. Thereafter, the probe assembly 103 may be traced over the target tissue object. As the probe is traced over the target tissue object and sensor data are recorded from the CCD 264, the position of the probe is tracked and recorded using, for example, the tracking system 500. Timed sensor data may then be mapped to a location on the 3D map. In some embodiments, a computer, such as the computer 420 may be programmed to receive sensor data from the probe at a period of time, to receive location information from the tracking system 500 for the period of time, and to map this data to corresponding points on the 3D map or mesh of the target object. In this manner, a location or coordinate value is associated with the timed sensor data.

As described above, co-registration is the process of aligning image data (of a plane or volume) with other image data and/or location data within the same coordinate space. Two types of co-registration techniques exist: intermodality and intramodality. Intermodality co-registration aligns image data of different modalities, whereas intramodality co-registration aligns image data from the same modality. Intermodality co-registration is beneficial because it enables the combination of multiple images (i.e., multiple image types) such that the advantageous characteristics of each are combined into a single image, enhancing the quality of the final image. Intramodality co-registration is beneficial because it enables the alignment of image data at different locations from the same modality such that the data can be used to determine the three-dimensional location of a point of interest or to reconstruct a volume. The disclosed method and system use intramodality co-registration to obtain co-registered, three-dimensional surface images from two-dimensional surface data. Of course, as used herein, the term "real-time" does not necessarily indicate that data and/or images are updated at the same rate or greater rate as the data and/or images are received. As used herein, use of the term "real-time" indicates a lack of significant delay or lag time, and may include embodiments in which data and/or images are updated at the same rate or greater rate as the data and/or images are received. For example, the term "real-time" may indicate that an action (e.g., data processing) or event (e.g., display of an image) occurs within in as much as several seconds from acquisition of the data, or may indicate that the action or event occurs within a second, or less than a second, from the data acquisition.

Co-registration of probe image data with a discretized 3D mesh mandates that the geometry of the probed 3D geometry (with which the image data is being co-registered) be known. The 3D geometry can be determined by a user's previous knowledge of the 3D geometry or by using a three-dimensional laser scanner (e.g., the 3D mesh generation assembly 410), which may automatically acquire the 3D geometry. Once the tracking system 500 provides the locations of the probe and the NIR image data are obtained using the NIR imaging system, the image data from each probe head 100A, 100B can be co-registered onto a discretized 3D mesh at the true location of the data.

The features of the NIR imager 101 described above allow the imager 101 to automatically determine, or at least estimate, the size of a target (e.g., a tumor) and the approximate or identify the location and/or boundaries of the target within the imaged tissue. The imager 101 is also operable to dynamically monitor and detect blood flow changes in the tissue. At the same time, the imager 101 is hand-held, light-weight, ultra-portable, and drastically less expensive than previous imaging technologies. The imager 101 is therefore, useful in many applications (as mentioned previously) including, but not limited to: breast cancer imaging (pre-screening, pre-operative, intra-operative, and post-operative); functional brain mapping; evaluation of finger arthritis/inflammation; wound healing; concussions (including on-site evaluation); sports injuries; pressure ulcerations; or generally many deep-tissue body imaging situations requiring immediate evaluation in the field or in a clinical setting, regardless of whether contact-based or non-contact based imaging is preferred. Because of the imager's non-contact operation, the imager can be used in intra-operative applications. For example, the imager can be used to help differentiate tumor margins during breast surgeries.

Reference throughout this specification to "one embodiment", "an embodiment", or a specific "embodiment" means that a particular feature, structure, or characteristic described in connection with the embodiment is included in at least one embodiment and not necessarily in all embodiments, and further, are not necessarily referring to the same embodiment. Furthermore, the particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention. By way of example, and not limitation, the present disclosure contemplates at least the following aspects:

1. An assembly forming a hand-held probe comprising:
a probe body;
a detector assembly comprising a detector operable to capture a focused, non-point image in the near infrared spectrum;
a source assembly comprising a near infrared light source; and
a tracking target;
wherein the near infrared light source is movable relative to the detector such that the probe can perform both reflectance and trans-illumination measurements.

2. The assembly of aspect 1 wherein the detector assembly is adjustably disposed within the probe body and movable along an optical axis of the detector assembly perpendicular to a surface to be imaged.

3. The assembly of aspect 1 wherein the detector assembly is adjustably disposed within a probe body and movable along an optical axis of the detector assembly such that the area of a surface to be imaged is variable.

4. The assembly of any of the preceding aspects, wherein the detector assembly further comprises one or more components selected from the group consisting of:
a lens assembly comprising a plurality of lenses;
a focusing lens; and
an optical filter.

5. The assembly of any of the preceding aspects, wherein the detector assembly further comprises a lens assembly, a focusing lens, and an optical filter.

6. The assembly of any of the preceding aspects, wherein the detector is a charge-coupled device.

7. The assembly of any of the preceding aspects, wherein the source assembly further comprises one or more components selected from the group consisting of:
   an optical filter;
   a collimation package; and
   a beam expander.
8. The assembly of any of the preceding aspects, wherein the source assembly further comprises an optical filter, a collimation package, and a beam expander.
9. The assembly of any of the preceding aspects, wherein the near infrared light source is an infrared light-emitting diode.
10. The assembly of any of the preceding aspects, wherein either or both of the source assembly and/or the detector assembly is modular to allow for one or more components to be replaced.
11. The assembly of any of the preceding aspects, the source assembly further comprises:
   a source module in which the near-infrared light source and any other optical components are disposed; and
   an elongated flexible member coupling the probe body to the source module;
   wherein the elongated flexible member facilitates positioning of the source module relative to the detector assembly.
12. The assembly of aspect 11, wherein the elongated flexible member is semi-rigid member operable to hold the source module in a selected position.
13. The assembly of any of the preceding aspects, further comprising a power source.
14. The assembly of any of the preceding aspects, further comprising a communication module.
15. The assembly of any one of the preceding aspects, wherein the communication module facilitates wireless communication.
16. The assembly of any of the preceding aspects, further comprising a control module.
17. The assembly of aspect 16, wherein the control module is operable to control the detector assembly and the source assembly, and to capture image data.
18. The assembly of aspect 16, wherein the control module is operable to capture image data from the detector assembly and to co-register the image data with a pre-loaded 3D mesh.
19. The assembly of any of the preceding aspects, wherein the source assembly removably attaches to the probe body at a source attachment point through which power and/or control signals pass.
20. The assembly of any of the preceding aspects, further comprising one or more actuators operable to adjust the position of the detector assembly.
21. The assembly of any one of aspects 1 to 20 wherein an inflexible arm is adjustable to move the light source into a first position for performing reflectance imaging and into a second position for performing trans-illumination imaging.
22. The assembly of any one of aspects 1 to 21, wherein the light source assembly further comprises multiple light sources.
23. The assembly of aspect 22, wherein the multiple light sources include light sources of varying wavelengths.
24. The assembly of any one of aspects 1 to 23, wherein the light source assembly comprises a white light source.
25. An imaging system comprising:
   the assembly of any of the preceding aspects;
   a processor configured to capture image data from the detector assembly and co-register the image data with a 3D mesh.
26. The imaging system of aspect 25, further comprising a 3D scanner for generating a 3D mesh of a target.
27. The imaging system of aspect 25 or aspect 26, further comprising a wired communication link between the processor and the hand-held probe.
28. The imaging system of aspect 27, wherein the wired communication link is a universal serial bus (USB) link.
29. The imaging system of either aspect 27 or aspect 28, wherein power to the hand-held probe is provided through the communication link.
30. The imaging system of aspect 25 or aspect 26, further comprising a wireless communication link between the processor and the hand-held probe.
31. The imaging system of any one of aspects 25 to 30, wherein the processor is further configured to provide a control function to the detector assembly and/or to the source assembly.

We claim:
1. An assembly forming a hand-held probe, comprising:
   a probe body;
   a detector assembly disposed within the probe body and comprising a detector operable to capture a focused, non-point image in the near infrared spectrum;
   a source assembly comprising a near infrared light source, the source assembly being separable from the detector assembly,
   wherein the near infrared light source is movable relative to the detector assembly and has a range of movement such that the hand-held probe can switch between diffuse reflectance and trans-illumination measurements while the probe body is maintained in the same position.
2. The assembly of claim 1 wherein the detector assembly is adjustably disposed within the probe body and movable along an optical axis of the detector assembly perpendicular to a surface to be imaged.
3. The assembly of claim 1 wherein the detector assembly is adjustably disposed within a probe body and movable along an optical axis of the detector assembly such that the area of a surface to be imaged is variable.
4. The assembly of claim 1, wherein the detector assembly further comprises a lens assembly, a focusing lens, and an optical filter.
5. The assembly of claim 1, wherein the source assembly further comprises an optical filter, a collimation package, and a beam expander.
6. The assembly of claim 1, wherein the near infrared light source is an infrared light-emitting diode.
7. The assembly of claim 1, wherein either or both of the source assembly and/or the detector assembly is modular to allow for one or more components to be replaced.
8. The assembly of claim 1, wherein the source assembly further comprises:
   a source module in which the near-infrared light source and any other optical components are disposed; and
   an elongated flexible member coupling the probe body to the source module;
   wherein the elongated flexible member facilitates positioning of the source module relative to the detector assembly.
9. The assembly of claim 8, wherein the elongated flexible member is semi-rigid member operable to hold the source module in a selected position.
10. The assembly of claim 1, wherein the tracking target is mounted to the probe body and is configured to provide tracking data indicative of a 3-dimensional (3D) position of the probe body as the probe body is moved throughout a region being imaged, and further comprising a processor operable to control the detector assembly and the source assembly, to (i) capture image data from the detector assembly, (ii) co-register the image data at probe positions indicated by the tracking data with a pre-loaded 3D mesh of the region being imaged, and (iii) display 3D image data once co-registered with the pre-loaded 3D mesh.

11. The assembly of claim 1, wherein the source assembly removably attaches to the probe body at a source attachment point through which power and/or control signals pass.

12. The assembly of claim 1, further comprising one or more actuators operable to adjust the position of the detector assembly.

13. The assembly of claim 1, wherein an adjustable handle assembly couples the source assembly to the detector assembly.

14. The assembly of claim 1, wherein the light source comprises (i) multiple light sources of varying wavelengths, or (ii) multi-wavelength light sources.

15. The assembly of claim 1, further comprising a communication link between a processor and the probe body, wherein power to the probe is provided through the communication link.

* * * * *